United States Patent
Ellis et al.

(10) Patent No.: US 8,632,573 B2
(45) Date of Patent: Jan. 21, 2014

(54) BONE FIXATION SYSTEM

(76) Inventors: Thomas J. Ellis, Dublin, OH (US); Joel Gillard, Portland, OR (US); Steven P. Horst, Dayton, OR (US)

(*) Notice: Subject to any disclaimer, the term of this patent is extended or adjusted under 35 U.S.C. 154(b) by 334 days.

(21) Appl. No.: 12/759,609

(22) Filed: Apr. 13, 2010

(65) Prior Publication Data

US 2010/0331844 A1   Dec. 30, 2010

Related U.S. Application Data

(63) Continuation of application No. 11/454,613, filed on Jun. 16, 2006, now Pat. No. 7,695,501, and a continuation-in-part of application No. 10/927,824, filed on Aug. 27, 2004, now Pat. No. 7,635,365.

(60) Provisional application No. 60/548,685, filed on Feb. 26, 2004, provisional application No. 60/498,866, filed on Aug. 28, 2003.

(51) Int. Cl.
    *A61B 17/80* (2006.01)
(52) U.S. Cl.
    USPC .................................. 606/280; 606/905
(58) Field of Classification Search
    USPC ............... 606/60, 248, 280–299, 74, 324, 606/900–905
    See application file for complete search history.

(56) References Cited

U.S. PATENT DOCUMENTS

| | | |
|---|---|---|
| 820,503 A | 5/1906 | Krengel et al. |
| 869,697 A | 10/1907 | Eilhauer et al. |
| 1,105,105 A | 7/1914 | Sherman |
| 1,156,440 A | 10/1915 | Smith |
| 1,345,425 A | 7/1920 | Wells |
| 1,789,060 A | 1/1931 | Weisenbach |
| 1,889,239 A | 11/1932 | Crowley |
| 1,950,799 A | 3/1934 | Jones |
| 2,406,832 A | 9/1946 | Hardinge |

(Continued)

FOREIGN PATENT DOCUMENTS

| | | |
|---|---|---|
| AU | 89750/91 | 2/1992 |
| CA | 2452127 | 12/1993 |

(Continued)

OTHER PUBLICATIONS

Lardinois et al. Pulmonary Function Testing After Operative Stabilisation of the Chest Wall for Flail Chest. *European Journal of Cardio-thoracic Surgery* (2001) 20:496-501.

(Continued)

*Primary Examiner* — Pedro Philogene
*Assistant Examiner* — Lynnsy Schneider
(74) *Attorney, Agent, or Firm* — Kolisch Hartwell, P.C.

(57) ABSTRACT

Device for fixing bone. In some embodiments, the device may comprise a plate member and a pair of hooks members. The plate member may have a pair of opposing edges arranged opposite each other. The pair of hook members each may project from a position adjacent the same edge of the plate member, to form a space to receive a same bone between the plate member and each of the hook members. Both hook members may be configured to contact a same side of the same bone. The plate member and a hook member may define first and second aligned apertures. The device also may comprise a fastener configured to extend from the first aperture, through the bone, and into locked engagement with the second aperture.

19 Claims, 10 Drawing Sheets

(56) References Cited

U.S. PATENT DOCUMENTS

| | | | |
|---|---|---|---|
| 2,443,363 A | 6/1948 | Townsend et al. | |
| 2,489,870 A | 11/1949 | Dzus | |
| 2,494,229 A | 1/1950 | Collison | |
| 2,496,126 A | 1/1950 | Haboush | |
| 2,500,370 A | 3/1950 | McKibbin | |
| 2,500,993 A | 3/1950 | Mason | |
| 2,526,959 A | 10/1950 | Lorenzo | |
| 2,579,968 A | 12/1951 | Rush | |
| 2,580,821 A | 1/1952 | Nicola | |
| 2,583,896 A | 1/1952 | Siebrandt | |
| 2,737,835 A | 3/1956 | Herz | |
| 3,025,853 A | 3/1962 | Mason | |
| 3,072,423 A | 1/1963 | Charlton | |
| 3,171,518 A | 3/1965 | Bergmann | |
| 3,244,170 A | 4/1966 | McElvenny | |
| 3,346,894 A | 10/1967 | Lemelson | |
| 3,357,432 A | 12/1967 | Sparks | |
| 3,386,437 A | 6/1968 | Treace | |
| 3,488,779 A | 1/1970 | Christensen | |
| 3,489,143 A | 1/1970 | Halloran | |
| 3,593,709 A * | 7/1971 | Halloran | 606/283 |
| 3,604,414 A | 9/1971 | Borges | |
| 3,716,050 A | 2/1973 | Johnston | |
| 3,726,279 A | 4/1973 | Barefoot et al. | |
| 3,741,205 A | 6/1973 | Markolf et al. | |
| 3,759,257 A | 9/1973 | Fischer et al. | |
| 3,774,244 A | 11/1973 | Walker | |
| 3,842,825 A | 10/1974 | Wagner | |
| 3,866,458 A | 2/1975 | Wagner | |
| 3,900,025 A | 8/1975 | Barnes, Jr. | |
| 3,901,064 A | 8/1975 | Jacobson | |
| 3,939,497 A | 2/1976 | Heimke et al. | |
| 3,965,720 A | 6/1976 | Goodwin et al. | |
| 4,000,525 A | 1/1977 | Klawitter et al. | |
| 4,011,863 A | 3/1977 | Zickel | |
| 4,055,172 A | 10/1977 | Ender et al. | |
| 4,091,806 A | 5/1978 | Aginski | |
| 4,119,092 A | 10/1978 | Gil | |
| 4,135,507 A | 1/1979 | Harris | |
| 4,169,470 A | 10/1979 | Ender et al. | |
| 4,187,840 A | 2/1980 | Watanabe | |
| 4,187,841 A | 2/1980 | Knutson | |
| 4,201,215 A | 5/1980 | Crossett et al. | |
| 4,263,904 A * | 4/1981 | Judet | 606/74 |
| 4,327,715 A * | 5/1982 | Corvisier | 606/71 |
| 4,364,382 A | 12/1982 | Mennen | |
| 4,378,607 A | 4/1983 | Wadsworth | |
| 4,388,921 A | 6/1983 | Sutter et al. | |
| 4,408,601 A | 10/1983 | Wenk | |
| RE31,628 E | 7/1984 | Allgower et al. | |
| 4,457,307 A | 7/1984 | Stillwell | |
| 4,473,069 A | 9/1984 | Kolmert | |
| 4,483,335 A | 11/1984 | Tornier | |
| 4,484,570 A | 11/1984 | Sutter et al. | |
| 4,493,317 A | 1/1985 | Klaue | |
| 4,503,847 A | 3/1985 | Mouradian | |
| 4,506,662 A | 3/1985 | Anapliotis | |
| 4,506,681 A | 3/1985 | Mundell | |
| 4,513,744 A | 4/1985 | Klaue | |
| 4,565,192 A | 1/1986 | Shapiro | |
| 4,565,193 A | 1/1986 | Streli | |
| 4,573,458 A | 3/1986 | Lower | |
| 4,630,601 A | 12/1986 | Harder et al. | |
| 4,651,724 A | 3/1987 | Berentey et al. | |
| 4,683,878 A | 8/1987 | Carter | |
| 4,703,751 A | 11/1987 | Pohl | |
| 4,718,413 A | 1/1988 | Johnson | |
| 4,730,608 A | 3/1988 | Schlein | |
| 4,733,654 A | 3/1988 | Marino | |
| 4,736,737 A | 4/1988 | Fargie et al. | |
| 4,743,261 A | 5/1988 | Epinette | |
| 4,750,481 A | 6/1988 | Reese | |
| 4,757,810 A | 7/1988 | Reese | |
| 4,759,350 A | 7/1988 | Dunn et al. | |
| 4,760,843 A | 8/1988 | Fischer et al. | |
| 4,794,918 A | 1/1989 | Wolter | |
| 4,800,874 A | 1/1989 | David et al. | |
| 4,823,780 A | 4/1989 | Odensten et al. | |
| 4,828,492 A | 5/1989 | Agnone | |
| 4,867,144 A | 9/1989 | Karas et al. | |
| 4,892,093 A | 1/1990 | Zarnowski et al. | |
| 4,893,619 A | 1/1990 | Dale et al. | |
| 4,896,661 A | 1/1990 | Bogert et al. | |
| 4,903,691 A | 2/1990 | Heinl | |
| 4,905,679 A | 3/1990 | Morgan | |
| 4,915,092 A | 4/1990 | Firică et al. | |
| 4,923,471 A | 5/1990 | Morgan | |
| 4,926,847 A | 5/1990 | Luckman | |
| 4,943,292 A | 7/1990 | Foux | |
| 4,955,886 A | 9/1990 | Pawluk | |
| 4,957,497 A | 9/1990 | Hoogland et al. | |
| 4,963,153 A | 10/1990 | Noesberger et al. | |
| 4,964,403 A | 10/1990 | Karas et al. | |
| 4,966,599 A | 10/1990 | Pollock | |
| 4,973,332 A | 11/1990 | Kummer | |
| 4,978,349 A | 12/1990 | Frigg | |
| 4,988,350 A | 1/1991 | Herzberg | |
| 5,002,544 A | 3/1991 | Klaue et al. | |
| 5,006,120 A | 4/1991 | Carter | |
| 5,013,314 A | 5/1991 | Firică et al. | |
| 5,013,315 A | 5/1991 | Barrows | |
| 5,015,248 A | 5/1991 | Burstein et al. | |
| 5,021,056 A | 6/1991 | Hofmann et al. | |
| 5,035,697 A | 7/1991 | Frigg | |
| 5,041,113 A | 8/1991 | Biedermann et al. | |
| 5,042,983 A | 8/1991 | Rayhack | |
| 5,049,149 A | 9/1991 | Schmidt | |
| 5,053,036 A | 10/1991 | Perren et al. | |
| 5,085,660 A | 2/1992 | Lin | |
| 5,113,685 A | 5/1992 | Asher et al. | |
| 5,116,335 A | 5/1992 | Hannon et al. | |
| 5,129,899 A | 7/1992 | Small et al. | |
| 5,133,718 A | 7/1992 | Mao | |
| 5,135,527 A | 8/1992 | Ender | |
| 5,139,497 A | 8/1992 | Tilghman et al. | |
| 5,147,361 A | 9/1992 | Ojima et al. | |
| 5,151,103 A | 9/1992 | Tepic et al. | |
| 5,161,404 A | 11/1992 | Hayes | |
| 5,176,685 A | 1/1993 | Rayhack | |
| 5,190,544 A | 3/1993 | Chapman et al. | |
| 5,190,545 A | 3/1993 | Corsi et al. | |
| 5,197,966 A | 3/1993 | Sommerkamp | |
| 5,201,736 A | 4/1993 | Strauss | |
| 5,201,737 A | 4/1993 | Leibinger et al. | |
| 5,234,431 A | 8/1993 | Keller | |
| 5,254,119 A | 10/1993 | Schreiber | |
| 5,261,908 A | 11/1993 | Campbell, Jr. | |
| 5,269,784 A | 12/1993 | Mast | |
| 5,290,288 A | 3/1994 | Vignaud et al. | |
| 5,304,180 A | 4/1994 | Slocum | |
| 5,314,490 A | 5/1994 | Wagner et al. | |
| 5,356,410 A | 10/1994 | Pennig | |
| 5,364,398 A | 11/1994 | Chapman et al. | |
| 5,364,399 A | 11/1994 | Lowery et al. | |
| 5,380,327 A | 1/1995 | Eggers et al. | |
| 5,413,577 A | 5/1995 | Pollock | |
| 5,413,579 A | 5/1995 | Du Toit | |
| 5,423,826 A | 6/1995 | Coates et al. | |
| 5,443,483 A | 8/1995 | Kirsch | |
| 5,443,516 A | 8/1995 | Albrektsson et al. | |
| 5,468,242 A | 11/1995 | Reisberg | |
| 5,474,553 A | 12/1995 | Baumgart | |
| 5,487,741 A | 1/1996 | Maruyama et al. | |
| 5,487,743 A | 1/1996 | Laurain et al. | |
| 5,522,902 A | 6/1996 | Yuan et al. | |
| 5,527,311 A | 6/1996 | Procter et al. | |
| 5,531,745 A | 7/1996 | Ray | |
| 5,534,027 A | 7/1996 | Hodorek | |
| 5,545,228 A | 8/1996 | Kambin | |
| 5,564,302 A | 10/1996 | Watrous | |
| 5,571,103 A | 11/1996 | Bailey | |
| 5,578,036 A | 11/1996 | Stone et al. | |
| 5,586,985 A | 12/1996 | Putnam et al. | |
| 5,591,166 A | 1/1997 | Bernhardt et al. | |

(56) References Cited

U.S. PATENT DOCUMENTS

| | | |
|---|---|---|
| 5,601,553 A | 2/1997 | Trebing et al. |
| 5,603,715 A | 2/1997 | Kessler |
| 5,607,426 A | 3/1997 | Ralph et al. |
| 5,643,261 A | 7/1997 | Schafer et al. |
| 5,643,265 A | 7/1997 | Errico et al. |
| 5,645,599 A | 7/1997 | Samani |
| 5,647,872 A | 7/1997 | Gilbert et al. |
| 5,658,283 A | 8/1997 | Huebner |
| 5,662,655 A | 9/1997 | Laboureau et al. |
| 5,665,088 A | 9/1997 | Gil et al. |
| 5,665,089 A | 9/1997 | Dall et al. |
| 5,674,222 A | 10/1997 | Berger et al. |
| 5,676,665 A | 10/1997 | Bryan |
| 5,676,667 A | 10/1997 | Hausman |
| 5,681,313 A | 10/1997 | Diez |
| 5,702,396 A | 12/1997 | Hoenig et al. |
| 5,707,372 A | 1/1998 | Errico et al. |
| 5,707,373 A | 1/1998 | Sevrain et al. |
| 5,709,682 A | 1/1998 | Medoff |
| 5,709,686 A | 1/1998 | Talos et al. |
| 5,718,704 A | 2/1998 | Medoff |
| 5,718,705 A | 2/1998 | Sammarco |
| 5,720,502 A | 2/1998 | Cain |
| 5,722,976 A | 3/1998 | Brown |
| 5,722,978 A | 3/1998 | Jenkins, Jr. |
| 5,730,743 A | 3/1998 | Kirsch et al. |
| 5,733,287 A | 3/1998 | Tepic et al. |
| 5,735,853 A | 4/1998 | Olerud |
| 5,741,258 A | 4/1998 | Klaue et al. |
| 5,741,259 A | 4/1998 | Chan |
| 5,749,872 A | 5/1998 | Kyle et al. |
| 5,749,873 A | 5/1998 | Fairley |
| 5,752,958 A | 5/1998 | Wellisz |
| 5,772,662 A | 6/1998 | Chapman et al. |
| 5,807,396 A | 9/1998 | Raveh |
| 5,810,823 A | 9/1998 | Klaue et al. |
| 5,810,824 A | 9/1998 | Chan |
| 5,814,047 A | 9/1998 | Emilio et al. |
| 5,853,413 A | 12/1998 | Carter et al. |
| D404,128 S | 1/1999 | Huebner |
| 5,855,580 A | 1/1999 | Kreidler et al. |
| 5,871,548 A | 2/1999 | Sanders et al. |
| 5,879,389 A | 3/1999 | Koshino |
| 5,902,304 A | 5/1999 | Walker et al. |
| 5,904,683 A | 5/1999 | Pohndorf et al. |
| 5,916,216 A | 6/1999 | DeSatnick et al. |
| 5,919,195 A | 7/1999 | Wilson et al. |
| 5,928,234 A | 7/1999 | Manspeizer |
| 5,931,839 A | 8/1999 | Medoff |
| 5,938,664 A | 8/1999 | Winquist et al. |
| 5,941,878 A | 8/1999 | Medoff |
| 5,951,557 A | 9/1999 | Luter |
| 5,954,722 A | 9/1999 | Bono |
| 5,964,763 A | 10/1999 | Incavo et al. |
| 5,968,046 A | 10/1999 | Castleman |
| 5,968,047 A | 10/1999 | Reed |
| 5,973,223 A | 10/1999 | Tellman et al. |
| 6,001,099 A | 12/1999 | Huebner |
| 6,004,323 A | 12/1999 | Park et al. |
| 6,004,353 A | 12/1999 | Masini |
| 6,007,535 A | 12/1999 | Rayhack et al. |
| 6,007,538 A | 12/1999 | Levin |
| 6,022,350 A | 2/2000 | Ganem |
| 6,027,504 A | 2/2000 | McGuire |
| 6,053,915 A | 4/2000 | Bruchmann |
| 6,077,266 A | 6/2000 | Medoff |
| 6,077,271 A | 6/2000 | Huebner et al. |
| 6,093,188 A | 7/2000 | Murray |
| 6,096,040 A | 8/2000 | Esser |
| 6,113,603 A | 9/2000 | Medoff |
| 6,117,139 A | 9/2000 | Shino |
| 6,117,160 A | 9/2000 | Bonutti |
| 6,123,709 A | 9/2000 | Jones |
| 6,129,728 A | 10/2000 | Schumacher et al. |
| 6,129,730 A | 10/2000 | Bono et al. |
| 6,139,548 A | 10/2000 | Errico |
| 6,152,927 A | 11/2000 | Farris et al. |
| 6,159,213 A | 12/2000 | Rogozinski |
| 6,179,839 B1 | 1/2001 | Weiss et al. |
| 6,183,475 B1 | 2/2001 | Lester et al. |
| 6,193,721 B1 | 2/2001 | Michelson |
| 6,197,028 B1 | 3/2001 | Ray et al. |
| 6,197,037 B1 | 3/2001 | Hair |
| 6,221,073 B1 | 4/2001 | Weiss et al. |
| 6,224,602 B1 | 5/2001 | Hayes |
| 6,228,087 B1 | 5/2001 | Fenaroli et al. |
| 6,235,033 B1 | 5/2001 | Brace et al. |
| 6,235,034 B1 | 5/2001 | Bray |
| 6,238,396 B1 | 5/2001 | Lombardo |
| 6,258,092 B1 | 7/2001 | Dall |
| 6,261,291 B1 | 7/2001 | Talaber et al. |
| 6,273,889 B1 | 8/2001 | Richelsoph |
| 6,280,446 B1 | 8/2001 | Blackmore |
| 6,283,969 B1 | 9/2001 | Grusin et al. |
| 6,290,703 B1 | 9/2001 | Ganem |
| 6,302,883 B1 | 10/2001 | Bono |
| 6,302,884 B1 | 10/2001 | Wellisz et al. |
| 6,302,887 B1 | 10/2001 | Spranza et al. |
| 6,306,136 B1 | 10/2001 | Baccelli |
| 6,312,431 B1 | 11/2001 | Asfora |
| 6,315,779 B1 | 11/2001 | Morrison et al. |
| 6,322,562 B1 | 11/2001 | Wolter |
| 6,325,803 B1 | 12/2001 | Schumacher et al. |
| 6,331,179 B1 | 12/2001 | Freid et al. |
| 6,336,927 B2 | 1/2002 | Rogozinski |
| 6,338,734 B1 | 1/2002 | Burke et al. |
| 6,342,055 B1 | 1/2002 | Eisermann et al. |
| 6,342,075 B1 | 1/2002 | MacArthur |
| 6,355,036 B1 | 3/2002 | Nakajima |
| 6,355,041 B1 | 3/2002 | Martin |
| 6,355,042 B2 | 3/2002 | Winquist |
| 6,358,250 B1 | 3/2002 | Orbay |
| 6,364,881 B1 | 4/2002 | Apgar et al. |
| 6,364,882 B1 | 4/2002 | Orbay |
| 6,364,883 B1 | 4/2002 | Santilli |
| 6,379,354 B1 | 4/2002 | Rogozinski |
| 6,379,359 B1 | 4/2002 | Dahners |
| 6,379,364 B1 | 4/2002 | Brace et al. |
| 6,402,756 B1 | 6/2002 | Ralph et al. |
| 6,413,259 B1 | 7/2002 | Lyons et al. |
| 6,428,542 B1 | 8/2002 | Michelson |
| 6,436,103 B1 | 8/2002 | Suddaby |
| 6,440,135 B2 | 8/2002 | Orbay et al. |
| 6,454,769 B2 | 9/2002 | Wagner et al. |
| 6,454,770 B1 | 9/2002 | Klaue |
| 6,458,133 B1 | 10/2002 | Lin |
| 6,503,250 B2 | 1/2003 | Paul |
| 6,508,819 B1 | 1/2003 | Orbay |
| 6,514,274 B1 | 2/2003 | Boucher et al. |
| 6,520,965 B2 | 2/2003 | Chervitz et al. |
| 6,527,775 B1 | 3/2003 | Warburton |
| 6,533,789 B1 | 3/2003 | Hall, IV et al. |
| 6,547,790 B2 | 4/2003 | Harkey et al. |
| 6,565,570 B2 | 5/2003 | Sterett et al. |
| 6,572,620 B1 | 6/2003 | Schon et al. |
| 6,592,578 B2 | 7/2003 | Henniges et al. |
| 6,595,993 B2 | 7/2003 | Donno et al. |
| 6,602,255 B1 | 8/2003 | Campbell et al. |
| 6,623,486 B1 | 9/2003 | Weaver et al. |
| 6,623,487 B1 | 9/2003 | Goshert |
| 6,682,531 B2 | 1/2004 | Winquist et al. |
| 6,682,533 B1 | 1/2004 | Dinsdale et al. |
| 6,689,139 B2 | 2/2004 | Horn |
| 6,695,846 B2 | 2/2004 | Richelsoph et al. |
| 6,706,046 B2 | 3/2004 | Orbay et al. |
| 6,712,820 B2 | 3/2004 | Orbay |
| 6,719,759 B2 | 4/2004 | Wagner et al. |
| 6,730,090 B2 | 5/2004 | Orbay et al. |
| 6,730,091 B1 | 5/2004 | Pfefferle et al. |
| 6,736,819 B2 | 5/2004 | Tipirneni |
| 6,767,351 B2 | 7/2004 | Orbay et al. |
| 6,793,658 B2 | 9/2004 | LeHuec et al. |
| 6,821,278 B2 | 11/2004 | Frigg et al. |
| 6,858,031 B2 | 2/2005 | Morrison et al. |

(56) References Cited

U.S. PATENT DOCUMENTS

| | | | |
|---|---|---|---|
| 6,863,694 B1* | 3/2005 | Boyce et al. | 623/23.63 |
| 6,866,665 B2 | 3/2005 | Orbay | |
| 6,893,444 B2 | 5/2005 | Orbay | |
| 6,955,677 B2 | 10/2005 | Dahners | |
| 6,974,461 B1 | 12/2005 | Wolter | |
| 7,011,659 B2* | 3/2006 | Lewis et al. | 606/276 |
| 7,070,600 B2* | 7/2006 | Silverman | 606/71 |
| 7,077,844 B2 | 7/2006 | Michelson | |
| 7,635,365 B2 | 12/2009 | Ellis et al. | |
| 7,695,501 B2 | 4/2010 | Ellis et al. | |
| 7,695,502 B2 | 4/2010 | Orbay et al. | |
| 7,727,264 B2 | 6/2010 | Orbay et al. | |
| 7,731,718 B2 | 6/2010 | Schwammberger et al. | |
| 2001/0011172 A1 | 8/2001 | Orbay et al. | |
| 2002/0004660 A1 | 1/2002 | Henniges et al. | |
| 2002/0032446 A1 | 3/2002 | Orbay | |
| 2002/0055741 A1 | 5/2002 | Schlapfer et al. | |
| 2002/0128654 A1 | 9/2002 | Steger et al. | |
| 2002/0143336 A1 | 10/2002 | Hearn | |
| 2002/0143337 A1 | 10/2002 | Orbay et al. | |
| 2002/0143338 A1 | 10/2002 | Orbay et al. | |
| 2002/0147453 A1 | 10/2002 | Gambale | |
| 2002/0151899 A1 | 10/2002 | Bailey et al. | |
| 2002/0156474 A1 | 10/2002 | Wack et al. | |
| 2002/0177852 A1 | 11/2002 | Chervitz et al. | |
| 2002/0183752 A1 | 12/2002 | Steiner et al. | |
| 2003/0040748 A1 | 2/2003 | Aikins et al. | |
| 2003/0055429 A1 | 3/2003 | Ip et al. | |
| 2003/0105461 A1 | 6/2003 | Putnam | |
| 2003/0149434 A1 | 8/2003 | Paul | |
| 2003/0153918 A1 | 8/2003 | Putnam et al. | |
| 2003/0233093 A1 | 12/2003 | Moles et al. | |
| 2004/0102775 A1 | 5/2004 | Huebner | |
| 2004/0102776 A1 | 5/2004 | Huebner | |
| 2004/0102777 A1 | 5/2004 | Huebner | |
| 2004/0102778 A1 | 5/2004 | Huebner et al. | |
| 2004/0116930 A1 | 6/2004 | O'Driscoll et al. | |
| 2004/0127901 A1 | 7/2004 | Huebner et al. | |
| 2004/0127903 A1 | 7/2004 | Schlapfer et al. | |
| 2004/0127904 A1 | 7/2004 | Konieczynski et al. | |
| 2004/0153073 A1 | 8/2004 | Orbay | |
| 2004/0186472 A1 | 9/2004 | Lewis et al. | |
| 2004/0193164 A1 | 9/2004 | Orbay | |
| 2004/0193165 A1 | 9/2004 | Orbay | |
| 2004/0220566 A1 | 11/2004 | Bray | |
| 2004/0260291 A1 | 12/2004 | Jensen | |
| 2004/0260292 A1 | 12/2004 | Orbay et al. | |
| 2004/0260293 A1 | 12/2004 | Orbay et al. | |
| 2004/0260294 A1 | 12/2004 | Orbay et al. | |
| 2004/0260295 A1 | 12/2004 | Orbay et al. | |
| 2005/0015089 A1 | 1/2005 | Young et al. | |
| 2005/0049593 A1 | 3/2005 | Duong et al. | |
| 2005/0065520 A1 | 3/2005 | Orbay | |
| 2005/0065522 A1 | 3/2005 | Orbay | |
| 2005/0065523 A1 | 3/2005 | Orbay | |
| 2005/0065524 A1 | 3/2005 | Orbay | |
| 2005/0065528 A1 | 3/2005 | Orbay | |
| 2005/0070902 A1 | 3/2005 | Medoff | |
| 2005/0085818 A1 | 4/2005 | Huebner | |
| 2005/0085819 A1 | 4/2005 | Ellis et al. | |
| 2005/0131413 A1 | 6/2005 | O'Driscoll et al. | |
| 2005/0159747 A1 | 7/2005 | Orbay | |
| 2005/0165395 A1 | 7/2005 | Orbay et al. | |
| 2005/0165400 A1 | 7/2005 | Fernandez | |
| 2005/0171544 A1* | 8/2005 | Falkner | 606/69 |
| 2005/0182405 A1 | 8/2005 | Orbay et al. | |
| 2005/0182406 A1 | 8/2005 | Orbay et al. | |
| 2005/0187551 A1 | 8/2005 | Orbay et al. | |
| 2005/0192578 A1 | 9/2005 | Horst | |
| 2005/0234458 A1 | 10/2005 | Huebner | |
| 2006/0085000 A1 | 4/2006 | Mohr et al. | |
| 2006/0100623 A1 | 5/2006 | Pennig | |
| 2007/0043367 A1 | 2/2007 | Lawrie | |
| 2007/0043368 A1 | 2/2007 | Lawrie et al. | |
| 2007/0083202 A1 | 4/2007 | Eli Running et al. | |
| 2007/0185493 A1 | 8/2007 | Feibel et al. | |
| 2007/0213727 A1 | 9/2007 | Bottlang et al. | |
| 2009/0177240 A1 | 7/2009 | Perez | |
| 2010/0234896 A1 | 9/2010 | Lorenz et al. | |
| 2010/0274245 A1 | 10/2010 | Gonzalez-Hernandez | |
| 2010/0331844 A1 | 12/2010 | Ellis et al. | |

FOREIGN PATENT DOCUMENTS

| | | |
|---|---|---|
| CH | 576249 | 6/1976 |
| CH | 611147 | 5/1979 |
| DE | 2515430 | 11/1975 |
| DE | 3808937 | 10/1989 |
| DE | 4201531 | 7/1993 |
| DE | 4343117 | 6/1995 |
| EP | 0053999 | 6/1982 |
| EP | 0029752 | 4/1983 |
| EP | 0094039 | 5/1983 |
| EP | 0179695 | 4/1986 |
| EP | 0410309 | 1/1991 |
| EP | 0415837 | 3/1991 |
| EP | 0471418 | 2/1992 |
| EP | 0362049 | 5/1992 |
| EP | 0561295 | 5/1996 |
| EP | 1250892 | 9/2003 |
| FR | 742.618 | 3/1933 |
| FR | 2211851 | 7/1974 |
| FR | 2254298 | 7/1975 |
| FR | 2367479 | 5/1978 |
| FR | 2405705 | 5/1979 |
| FR | 2405706 | 5/1979 |
| FR | 2406429 | 5/1979 |
| FR | 2416683 | 9/1979 |
| FR | 2472373 | 7/1981 |
| FR | 2674118 | 9/1992 |
| GB | 2245498 | 1/1992 |
| GB | 2331244 | 5/1999 |
| GB | 2435429 | 8/2007 |
| JP | S47-44985 | 0/1972 |
| JP | S64-032855 A | 2/1989 |
| JP | H05-146502 A | 6/1993 |
| JP | H06-3551 Y2 | 2/1994 |
| JP | 2002-542875 | 12/2002 |
| SU | 610518 | 6/1978 |
| SU | 718097 | 2/1980 |
| SU | 862937 | 9/1981 |
| SU | 874044 | 10/1981 |
| SU | 897233 | 1/1982 |
| SU | 921553 | 4/1982 |
| SU | 1049054 | 10/1983 |
| SU | 1130332 | 12/1984 |
| SU | 1192806 | 11/1985 |
| SU | 1223901 | 4/1986 |
| SU | 1225556 | 4/1986 |
| SU | 1544406 | 2/1990 |
| SU | 1630804 | 2/1991 |
| SU | 1644932 | 4/1991 |
| SU | 1683724 | 10/1991 |
| SU | 1711859 | 2/1992 |
| SU | 1734715 | 5/1992 |
| WO | WO82/01645 | 5/1982 |
| WO | WO87/02572 | 5/1987 |
| WO | WO88/03781 | 6/1988 |
| WO | WO95/05782 | 3/1995 |
| WO | WO96/29948 | 10/1996 |
| WO | WO97/47251 | 12/1997 |
| WO | WO99/22089 | 5/1999 |
| WO | WO01/21083 | 3/2001 |
| WO | WO01/62136 | 8/2001 |
| WO | WO02/03882 | 1/2002 |
| WO | WO03/105712 | 12/2003 |
| WO | WO2007/092813 | 8/2007 |
| WO | 2007/109436 A2 | 9/2007 |

OTHER PUBLICATIONS

Legacy Biomechanics Laboratory, *Applied Research*, Jan. 2006, original website <http://www.biomechresearch.org/sling.html>, viewable via the Internet Archive Wayback Machine <http://replay.

(56) References Cited

OTHER PUBLICATIONS waybackmachine.org/20060320091922/http://www.biomechresearch.org/sling.html>.
Leung et al., Palmar Plate Fixation of AO Type C2 Fracture of Distal Radius Using a Locking Compression Plate—A Biomechanical Study in a Cadaveric Model, *Journal of Hand Surgery*, vol. 28B, No. 3, pp. 263-266, Jun. 2003.
Martin GmbH & Co. KG, Bilder internet printout, print date Sep. 5, 2003.
Mayberry, Absorable Plates for Rib Fracture Repair: Preliminary Experience, *Journal of Trauma Injury, Infection and Critical Care.* vol. 55, No. 5, pp. 835-839, Nov. 2003.
Mizuho Co., Ltd., Jplate Diaphysis Plates for Japanese brochure, 2002.
Moore et al., *Clinically Oriented Anatomy*, Fourth Edition, pp. 70-71, 2004.
Moore et al., Operative stabilization of nonpenetrating chest injuries, *The Journal of Thoracic and Cardiovascular Surgery*, vol. 70, No. 4, p. 619-630, 1975.
Morgan et al., Salvage of Tibial Pilon Fractures Using Fusion of the Ankle with a 90° Cannulated blade Plate: A Preliminary Report, *Foot & Ankle International*, vol. 20, No. 6, pp. 375-378, Jun. 1999.
Ng et al. Operative Stabilisation of Painful Non-united Multiple Rib Fractures. *Injury* (2001) 32:637-639.
Nunley et al., Delayed Rupture of the Flexor Pollicis Longus Tendon After Inappropriate Placement of the π Plate on the Volar Surface of the Distal Radius, *Journal of Hand Surgery*, vol. 24, No. 6, pp. 1279-1280, Nov. 1999.
Orthocopia, LLC, Synthes Volar Distal Radius Locking Plate internet description page, 2004.
Osada et al., Comparison of Different Distal Radius Dorsal and Volar Fracture Fixation Plates: A Biomechanical Study, *Journal of Hand Surgery*, vol. 28A, No. 1, pp. 94-104, Jan. 2003.
Osteomed, images of *Resorable Plates*, Feb. 2006 <http://www.osteomedcorp.com/images/library/resorbfixation.gif>.
Oyarzun et al. Use of 3.5mm Acetabular Reconstruction Plates for Internal Fixation of Flail Chest Injuries, *Section of Cardiothoracic Surgery*, pp. 1471-1474, 1998.
Palmer et al., The Use of Interlocked 'Customised' Blade Plates in the Treatment of Metaphyseal Fractures in Patients with Poor Bone Stock, *Injury, Int. J. Care Injured*, vol. 31, pp. 187-191, 2002.
Peine et al., Comparison of Three Different Plating Techniques for the Dorsum of the Distal Radius: A Biomechanical Study, *Journal of Hand Surgery*, vol. 25A, No. 1, pp. 29-33, Jan. 2000.
Putnam et al., Distal Radial Metaphyseal Forces in an Extrinsic Grip Model: Implications for Postfracture Rehabilitation, *Journal of Hand Surgery*, vol. 25A, No. 3, pp. 469-475, May 2000.
Reip, David, Authorized officer, International Searching Authority, International Search Report for PCT Patent Application Serial No. PCT/US03/22904, Dec. 4, 2003.
Ring et al., Prospective Multicenter Trial of a Plate for Dorsal Fixation of Distal Radius Fractures, *The Journal of Hand Surgery*, vol. 22A, No. 5, pp. 777-784, Sep. 1997.
Rozental et al., Functional Outcome and Complications Following Two Types of Dorsal Plating for Unstable Fractures of the Distal Part of the Radius, *Journal of Bone and Joint Surgery*, vol. 85, No. 10, pp. 1956-1960, 2003 (abstract only).
Ruch et al., Results of Palmar Plating of the Lunate Facdet Combined with External Fixation for the Treatment of High-Energy Compression Fractures of the Distal Radius, *J. Orthop. Trauma*, Vo. 18, No. 1, pp. 28-33, Jan. 2004.
Sanatmetal, *Rib Securing Clamped Plate*, internet printout, Sep. 2004 <http://www.sanatmetal.hu/catalog/pict/1_5_89a_1.jpg>.
Sanchez-Sotelo et al., Principle-Based Internal Fixation of Distal Humerus Fractures, *Techniques in Hand & Upper Extremity Surgery*, vol. 5, No. 4, pp. 179-187, Dec. 2001.
Simic, Fractures of the Distal Aspect of the Radius: Changes in Treatment Over the Past Two Decades, *Journal of Bone and Joint Surgery*, vol. 85-A, No. 3, pp. 552-564, Mar. 2003.

Slater et al. Operative Stabilization of Flail Chest Six Years After Injury. *Annals of Thoracic Surgery* Aug. 2001:600-601.
Stryker SmartLock Locking Screw Technology, advertisement, *The Journal of Hand Surgery*, vol. 30A, No. 1, Jan. 2005.
Surfix Technologies, Single Units Osteosynthesis brochure, Sep. 2000.
Synthes (USA), 3.5 mm LCP™ Proximal Humerus Plate technique guide, 2002.
Synthes (USA), *Biological Plating: A New Concept to Foster Bone Healing*, 1991.
Synthes (USA), The Distal Radius Plate Instrument and Implant Set technique guide, 1999.
Synthes (USA), The Titanium Distal Radius Plate, technique guide, 1997.
Synthes (USA), Titanium Distal Radius Plates description page, 2001.
Synthes, Small Titanium Plates overview page, p. 2a-33, Mar. 1997.
Synthes, Titanium Distal Radius Instrument and Implant Set standard contents description pages, Mar. 1997.
Tanaka et al. Surgical Stabilization or Internal Pneumatic Stabilization? A Prospective Randomized Study of Management of Severe Flail Chest Patients. *Journal of Trauma* (2002) 52:727-732.
Tarazona et al., *Surgical stabilization of traumatic flail chest*, pp. 521-527, 1975.
Tatsumi et al., Bioabsorable Poly-L-Lactide Costal Coaptation Pins and Their Clinical Application in Thoroacotomy, *Original Articles: General Thoracic.* pp. 765-768, 1999.
Techmedica, Inc., Techmedica Bioengineers Keep Tabs on Your Needs brochure, 1991.
Techmedica, Inc., The Arnett-TMP* Titanium Miniplating System brochure, 1989.
Thomas et al., Operative stabilization for flail chest after blunt trauma, *The Journal of Thoracic and Cardiovascular Surgery*, vol. 75, No. 6, pp. 793-801, 1978.
Toby, *Scaphoid Protocols Using the Acutrak® Bone Screw System* brochure, published by Acumed, Inc., Dec. 7, 1999.
Tornetta, Distal Radius Fracture, *Journal of Orthopaedic Trauma*, vol. 16, No. 8, pp. 608-611, 2002.
Trimed Inc., *TriMed Wrist Fixation System* brochure, 1997.
Trimed Inc., *TriMed Wrist Fixation System* internet description pages, 2001.
Trumble et al., Intra-Articular Fractures of the Distal Aspect of the Radius, *Journal of Bone and Joint Surgery*, vol. 80A, No. 4, pp. 582-600, Apr. 1998.
Trunkey, Chest Wall Injuries, *Cerviothoracic Trauma*, vol. 3. pp. 129-149, 1986.
Turner et al., *Tendon Function and Morphology Related to Material and Design of Plates for Distal Radius Fracture Fixation: Canine Forelimb Model*, Orthopaedic Research Society, Feb. 2003.
US Implants, Val Plate description page, undated.
Vitallium, Bone Plates brochure, Mar. 1948.
Abel et al., An Axially Mobile Plate for Fracture Fixation, *Internal Fixation in Osteoporotic Bone*, pp. 279-283, 2002.
Ace Medical Company, Ace 4.5/5.0 mm Titanium Cannulated Screw and Reconstruction Plate System simplified fracture fixation brochure, 1992.
Ace Medical Company, Ace 4.5/5.0 mm Titanium Cannulated Screw and Reconstruction Plate System surgical technique brochure, 1992.
Ace Medical Company, Ace Symmetry Titanium Upper Extremity Plates surgical technique brochure, 1996.
Ace Medical Company, Ace Titanium 3.5/4.0 mm Screw and Plate System with the Ace 3.5 mm Universal Ribbon CT/MRI compatible fixation brochure, 1992.
Ace Medical Company, The Ace Symmetry Titanium Upper Extremity Plates new product release brochure, 1996.
Acromio-Clavicular Plates description page, author and date unknown.
Acumed Inc., Congruent Distal Radius Plate System description, Mar. 4, 1998.
Acumed Inc., Congruent Plate System—The Mayo Clinic Congruent Elbow Plates brochure, May 7, 2002.
Acumed Inc., Modular Hand System brochure, Aug. 2002.
Acumed Inc., Modular Hand System brochure, Sep. 2002.

(56) References Cited

OTHER PUBLICATIONS

Amadio, Open Reduction of Intra-Articular Fractures of the Distal Radius, *Fractures of the Distal Radius*, pp. 193-202, 1995.
An, Y.H., *Internal Fixation in Osteoporotic Bone*, pp. 82-83, 2002.
Avanta Orthopaedics, SCS/D Distal Radius Plate System brochure, 1997.
Avanta Orthopaedics, SCS/V Distal Radius Plate Volar brochure, 1998.
Beaupre et al., A Comparison of Unicortical and Bicortical End Screw Attachment of Fracture Fixation Plates, *Journal of Orthopaedic Trauma*, vol. 6, No. 3, pp. 294-300, 1992.
Biomet Orthopedics, Inc., Supracondylar Cable Plate brochure, 2000.
Cacchione et al., Painful Nonunion of Multiple Rib Fractures Managed by Operative Stabilization, *The Journal of Trauma, Injury, Infection and Critical Care*, vol. 48, No. 2, pp. 319-321, 2000.
Chin et al., Salvage of Distal Tibia Metaphyseal Nonunions With the 90° Cannulated Blade Plate, *Clinical Orthopaedics and Related Research*, No. 409, pp. 241-249, 2003.
Codman & Shurtleff, Inc., Zuelzer Hook Plates description page, p. 808, undated.
Copenheaver, Blaine R., Authorized officer, International Searching Authority, U.S. Patent and Trademark Office, International Search Report, PCT Application Serial No. PCT/US2006/027805; search completion date: Dec. 1, 2006; mail date: Jan. 31, 2007.
Copenheaver, Blaine R., Authorized officer, International Searching Authority, U.S. Patent and Trademark Office, Written Opinion of the International Searching Authority, PCT Application Serial No. PCT/US2006/027805; opinion completion date: Dec. 1, 2006; mail date: Jan. 31, 2007.
DePuy Ace, *TiMAX Pe.R.I. Small Fragment Upper Extremity* description pages, 1999.
DePuy, Inc., McBride S.M.O. Stainless Steel Bone Plates brochure, 1943.
Ducloyer, *Treatment by Plates of Anteriorly Displaced Distal Radial Fractures*, Fractures of the Distal Radius, pp. 148-152, 1995.
European Patent Office, Supplementary European Search Report, European Patent Application Serial No. EP 03786953.4; search completion date: Mar. 19, 2010; mail date: Mar. 29, 2010.
DVO Extremity Solutions, MIfx Dorsal IM Plate, brochure, Sep. 2005.
Engel et al., Operative Chest Wall Fixation with Osteosynthesis Plates, *The Journal of Trauma, Injury, Infection and Critical Care*, vol. 58, No. 1, pp. 181-186, 2005.
Erothitan Titanimplantate AG, Titanium Wire Plate Osteosynthesis System According to Dr. Gahr internet printout, print date Feb. 6, 2003.
Esser Complete Distal Radius Plate System, undated.
Esser, Proximal Humerus Fractures operative technique, undated.
Esser, Treatment of Three- and Four-Part Fractures of the Proximal Humerus with a Modified Cloverleaf Plate, *Journal of Orthopaedic Trauma*, vol. 8, No. 1, pp. 15-22, 1994.
Fernandez et al., *Fractures of the Distal Radius: A Practical Approach to Management*, pp. 103-188, 1996.
Fitoussi et al., Treatment of Displaced Intra-Articular Fractures of the Distal End of the Radius With Plates, *The Journal of Bone and Joint Surgery*, vol. 79, No. 9, pp. 1303-1312, 1997 (abstract only provided).
European Patent Office, Communication Pursuant to article 94(3) EPC, European Patent Application No. 04782685.4; dated Feb. 9, 2011.
European Patent Office, Supplementary European Search Report, European Patent Application No. 04782685.4; dated Oct. 10, 2008.
Gesensway et al., Design and Biomechanics of a Plate for the Distal Radius, *Journal of Hand Surgery*, vol. 20, No. 6, pp. 1021-1027, 1995 (abstract only provided).
Haasler, Open Fixation of Flail Chest After Blunt Trauma, *The Society of Thoracic Surgeons*, pp. 993-995, 1990.
Harvey et al., The Use of a Locking Custom Contoured Blade Plate for Peri-Articular Nonunions, *Injury, Int. J. Care Injured*, vol. 34, pp. 111-116, 2003.
Hooker et al., *Fixation of Unstable Fractures of the Volar Rim of the Distal Radius with a Volar Buttress Pin®*, 2003.
Howmedica Inc., Dupont Distal Humeral Plates brochure, 1990.
U.K. Intellectual Property Office, Patents Act 1977: Combined Search and Examination Report under Sections 17 and 18(3), United Kingdom Patent Application No. GB0810872.2; search date: Sep. 4, 2008.
Jupiter et al., Management of Comminuted Distal Radial Fractures, *Fractures of the Distal Radius*, pp. 167-183, 1995.
Kambouroglou et al., Complications of the AO/ASIF Titanium Distal Radius Plate System ($\pi$ Plate) in Internal Fixation of the Distal Radius: A Brief Report, *Journal of Hand Surgery*, vol. 23A, No. 4, pp. 737-741, Jul. 1998.
Kinetics Medical Incorporated, Spider™ and Mini-Spider™ Limited Wrist Fusion System brochure, undated.
Kinetics Medical Incorporated, Spider™ Limited Wrist Fusion System brochure, undated.
Klein et al., *Rib Fracture Healing after Osteosynthesis with Wire Mesh Titanium and Screws: A Histological Study in Sheep*, pp. 347-354, 1989.
Kolodziej et al., Biomechanical Evaluation of the Schuhli Nut, *Clinical Orthopaedics and Related Research*, vol. 347, pp. 79-85, Feb. 1998.
Konrath et al., Open Reduction and Internal Fixation of Unstable Distal Radius Fractures: Results Using the Trimed Fixation System, *Journal of Orthopaedic Trauma*, vol. 16, No. 8, pp. 578-585, 2002.
Landreneau et al., Strut Fixation of an Extensive Flail Chest, *The Society of Thoracic Surgeons*, pp. 473-475, 1991.
Voggenreiter et al., Operative Chest Wall Stabilization in Flail Chest—Outcomes of Patients With or Without Pulmonary Contusion, *American College of Surgeons*, pp. 130-138, 1998.
Waldemar Link GmbH & Co., May Anatomical Bone Plates: Plates, Bone Screws and Instruments brochure, pp. 3-4 and 10-15, 1995.
Wright Medical Technology, Inc., Locon-T Distal Radius Plating System case study and surgical method, 2001.
Wright Medical Technology, Inc., Locon-T Distal Radius Plating System brochure, 2002.
Young, Outcome Following Nonoperative Treatment of Displaced Distal Radius Fractures in Low-Demand Patients Older Than 60 Years, *Journal of Hand Surgery*, vol. 25A, No. 1, pp. 19-28, Jan. 2000.
Zespol Bone Plates, in *Mikromed—Catalogue 2004* (Nov. 2004), original website <http://www.mikromed.pl/katalog/Main/main_eng.htm> and <http://www.mikromed.pl/katalog/zespol_eng/plytki.htm>, viewable via the Internet Archive Wayback Machine <http://replay.waybackmachine.org/20070830023439/http;://www.mikromed.pl/katalog/zespol_eng/plytki.htm>.
Zespol Bone Screws, in *Mikromed—Catalogue 2004* (Nov. 2004), original website <http://www.mikromed.pl/katalog/Main/main_eng.htm> and <http://www.mikromed.pl/katalog/zespol_eng/wkrety.htm>, viewable via the Internet Archive Wayback Machine <http://replay.waybackmachine.org/20050226124226/http://www.mikromed.pl/katalog/zespol_eng/wkrety.htm>.
Zimmer, Inc., ECT Internal Fracture Fixation brochure, undated.
Zimmer, Inc., ECT Internal Fracture Fixation System order information brochure, undated.
Zimmer, Inc., Forte Distal Radial Plate System brochure, 1995.
Zimmer, Inc., NexGen Osteotomy System (OS) surgical technique brochure, undated.
Zimmer, Inc., Periarticular Plating System brochure, 2002.
"Notice of Reasons for Rejection" in connection with corresponding Japanese Patent Application No. 2011-088250, Sep. 20, 2012, 4 pages.
AO Foundation, TK System Innovations, Dec. 2011, 60 pages.
Japan Patent Office, Office Action regarding Japanese Patent Application No. 2011-088250, dated Jan. 29, 2013, 6 pages.

\* cited by examiner

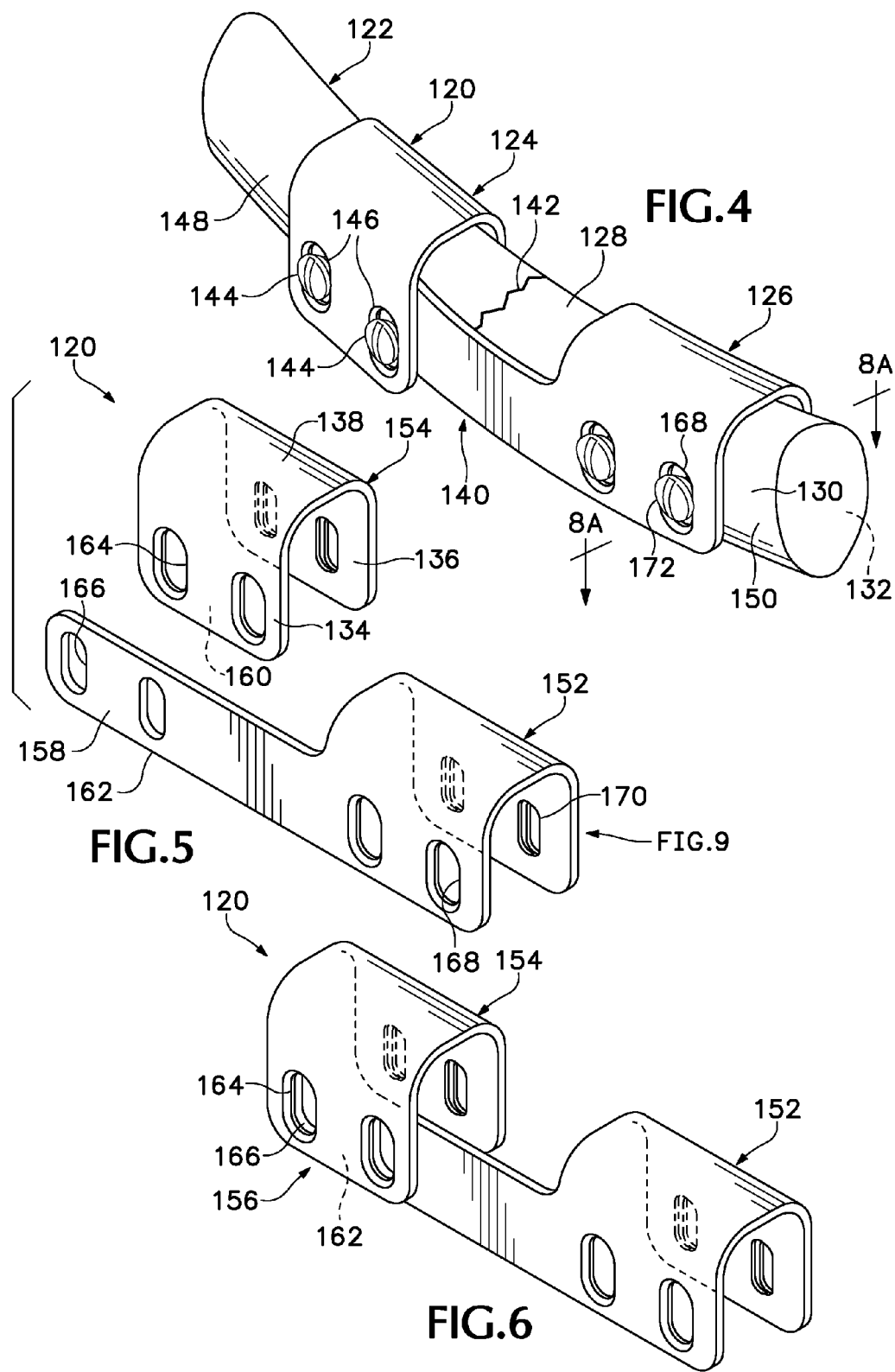

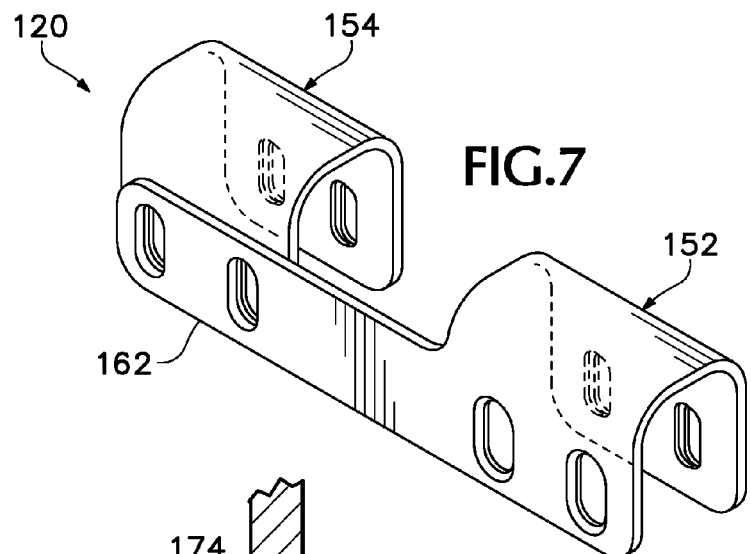
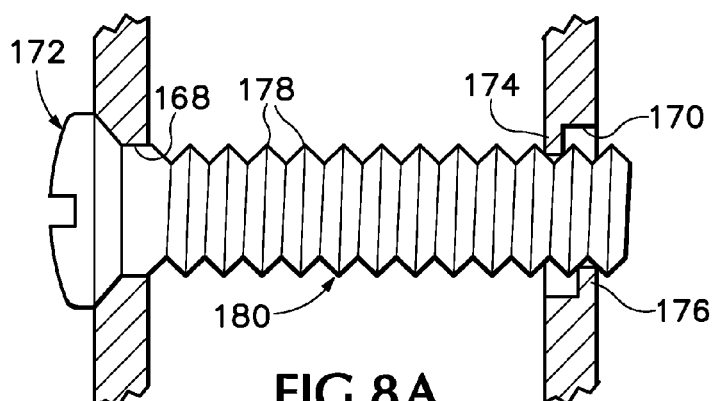
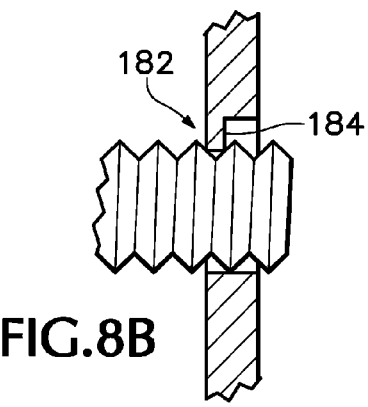
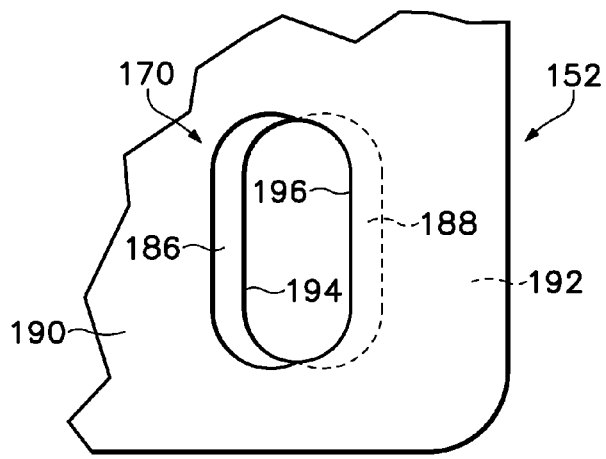

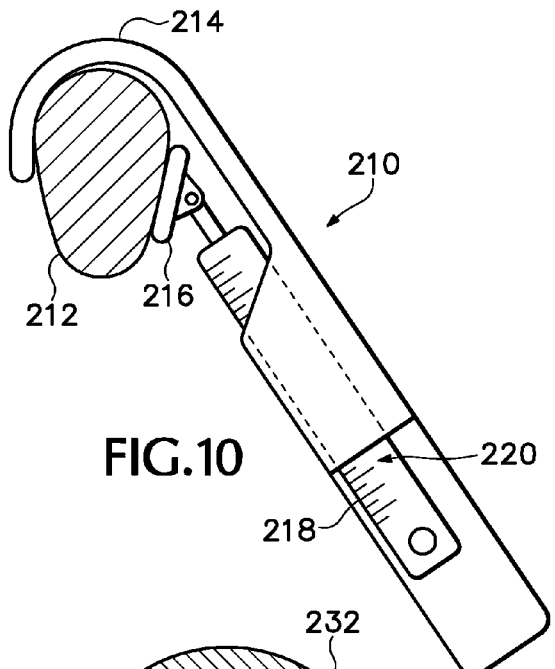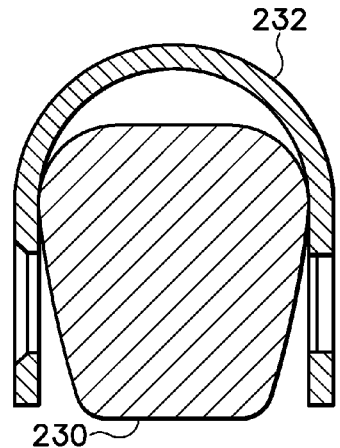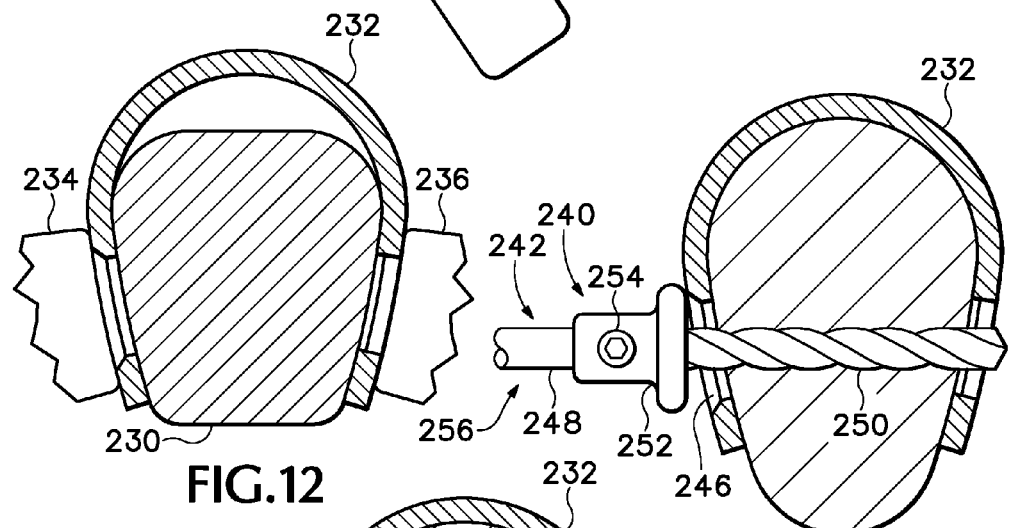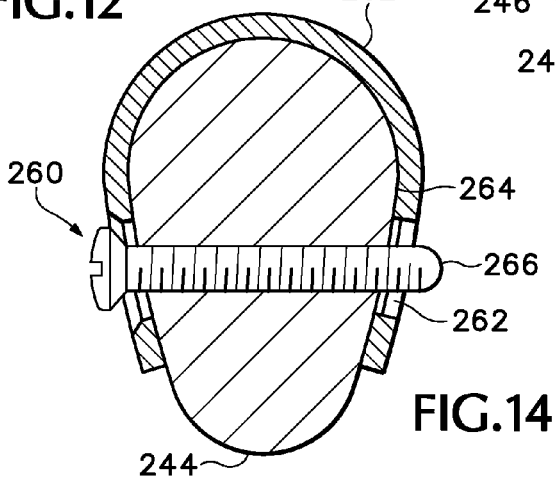

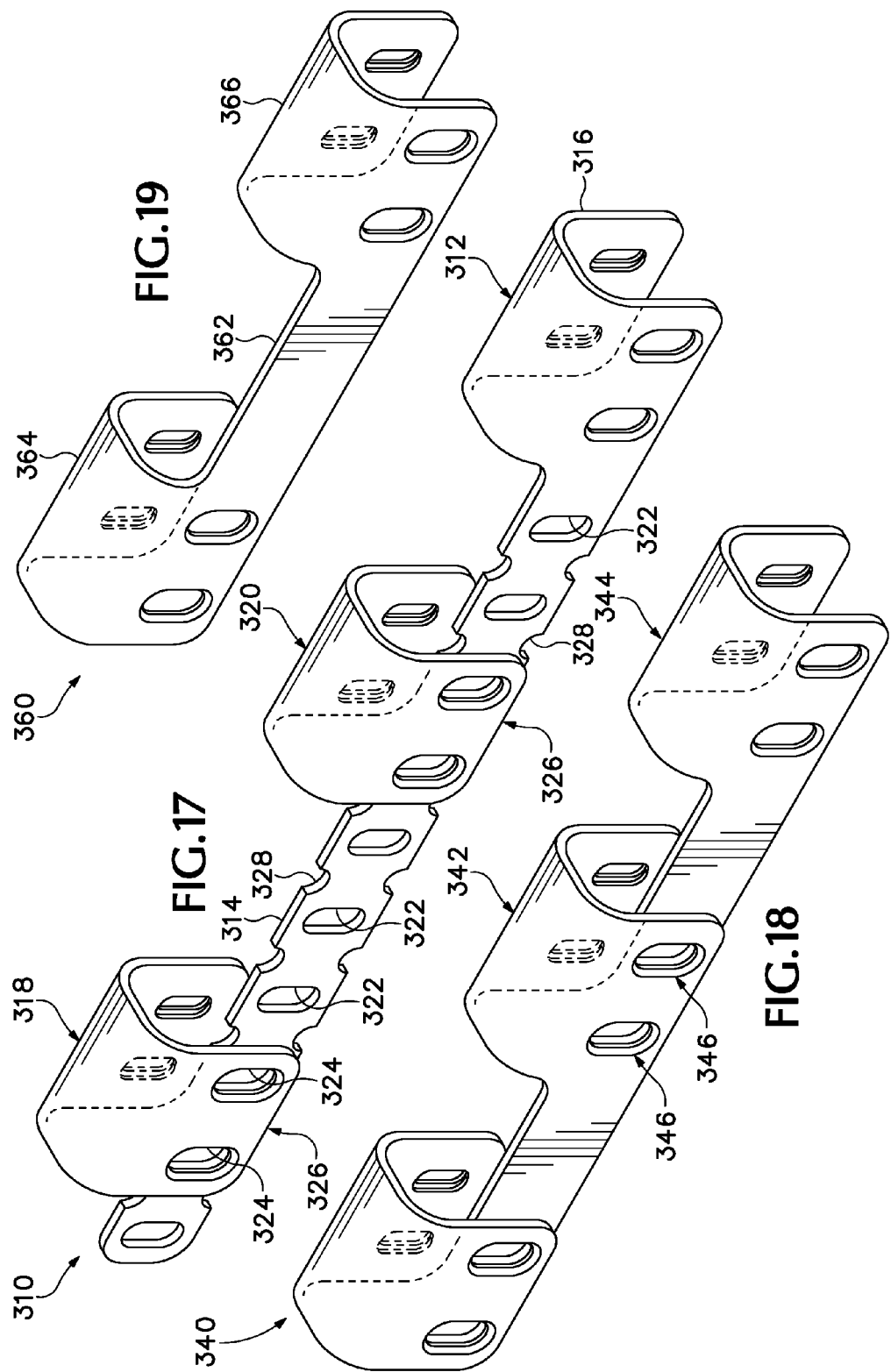

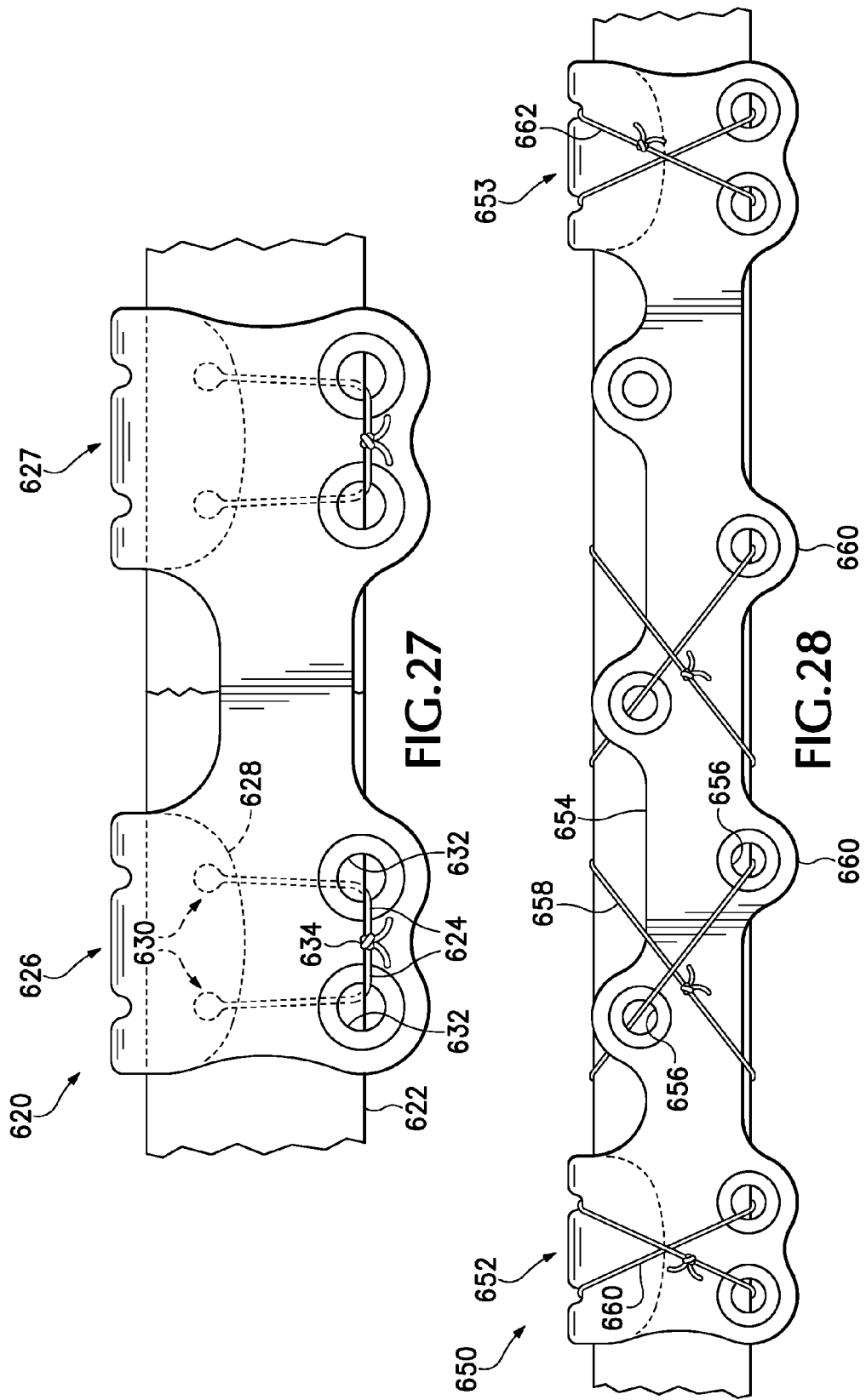

BONE FIXATION SYSTEM

CROSS-REFERENCES TO PRIORITY APPLICATIONS

This application is a continuation of U.S. patent application Ser. No. 11/454,613, filed Jun. 16, 2006, now U.S. Pat. No. 7,695,501, which, in turn, is a continuation-in-part of U.S. patent application Ser. No. 10/927,824, filed Aug. 27, 2004, now U.S. Pat. No. 7,635,365, which, in turn, is based upon and claims the benefit under 35 U.S.C. §119(e) of the following U.S. provisional patent applications: Ser. No. 60/548,685, filed Feb. 26, 2004; and Ser. No. 60/498,866, filed Aug. 28, 2003. Each of the above-cited applications is incorporated herein by reference in its entirety for all purposes.

BACKGROUND

The human skeleton is composed of 206 individual bones that perform a variety of important functions, including support, movement, protection, storage of minerals, and formation of blood cells. These bones can be grouped into two categories, the axial skeleton and the appendicular skeleton. The axial skeleton consists of 80 bones that make up the body's center of gravity, and the appendicular skeleton consists of 126 bones that make up the body's appendages. The axial skeleton includes the skull, vertebral column, ribs, and sternum, among others, and the appendicular skeleton includes the long bones of the upper and lower limbs, and the clavicles and other bones that attach these long bones to the axial skeleton, among others.

To ensure that the skeleton retains its ability to perform its important functions, and to reduce pain and disfigurement, fractured bones should be repaired promptly and properly. Typically, fractured bones are treated using fixation devices, which reinforce the fractured bones and keep them aligned during healing. Fixation devices may take a variety of forms, including casts for external fixation and bone plates for internal fixation, among others. Casts are minimally invasive, allowing reduction and fixation of simple fractures from outside the body. In contrast, bone plates are internal devices that mount under the skin of a plate recipient and directly to bone to span a fracture.

Trauma to the torso may result in fracture of one or more ribs. Frequently, a simple rib fracture is nondisplaced, so that reduction and/or internal fixation of the fracture may not be required. However, in cases of more severe trauma to the chest, a single rib may be fractured more severely and/or multiple rib fractures may occur. With multiple rib fractures, a section of the thoracic wall may become detached from the rest of the chest wall, a condition known to medical practitioners as "flail chest". A flail chest condition often results in paradoxical motion of the injured area, in which the freely floating thoracic section is drawn in during inspiration, and pushed out during expiration. This condition may result in severe respiratory distress, possibly requiring the patient to be sedated and/or intubated during early stages of healing. Fixing single or multiple rib fractures internally may alleviate paradoxical motion, reduce pain, and/or help to prevent secondary injuries.

Internal fixation of a rib fracture may be accomplished using a bone plate to span the fracture. A bone plate suitable for treating fractured ribs may be custom-contoured (i.e., bent) by a surgeon to conform to a region of a rib spanning a fracture, and then fastened to the rib on both sides of the fracture. The plate thus fixes the rib to permit healing. The plate may be fastened to the fractured rib using fasteners, such as bone screws, wires, and/or suture material, among others. Alternatively, a bone plate may be used that has prongs disposed along its length. The prongs may be crimped so that they grasp the rib to fasten the bone plate to the rib.

Each of these plating techniques may have disadvantages for rib fixation. For example, some or all of these techniques may not sufficiently stabilize the rib to provide adequate flexural and torsional support for the rib at the fracture site. Alternatively, or in addition, some or all of these techniques may be too slow for installation of bone plates in trauma patients.

SUMMARY

The present teachings provide systems, including methods, apparatus, and kits, for fixing bones, such as rib bones, with bone plates.

BRIEF DESCRIPTION OF THE DRAWINGS

FIG. 4 is a view of a second embodiment of an exemplary bone plate secured to and fixing a fractured rib bone, in accordance with aspects of the present teachings.

FIG. 5 is an exploded view of the bone plate of FIG. 4 in the absence of the rib bone.

FIG. 6 is a view of an exemplary assembled configuration for components of the bone plate of FIG. 4, in the absence of the rib bone and fasteners, in accordance with aspects of the present teachings.

FIG. 7 is a view of an alternative exemplary assembled configuration for the components of the bone plate of FIG. 4, in the absence of the rib bone and fasteners, in accordance with aspects of the present teachings.

FIG. 8A is a fragmentary sectional view of the bone plate of FIG. 4 without the rib bone, taken generally along line 8A-8A of FIG. 4, and illustrating a bone screw extending through a pair of aligned plate apertures including an exemplary locking aperture, in accordance with aspects of the present teachings.

FIG. 8B is a fragmentary sectional view of another exemplary locking aperture engaged with a bone screw, in accordance with aspects of the present teachings.

FIG. 9 is a view of a portion of the bone plate of FIGS. 4-7, as indicated in FIG. 5, and including the locking aperture of the pair of apertures of FIG. 8A, in accordance with aspects of the present teachings.

FIG. 10 is a partially sectional view of bone calipers being used to measure the thickness of a rib bone, in accordance with aspects of the present teachings.

FIG. 11 is a sectional view of a hook component of a bone plate received on a bending die, in accordance with aspects of the present teachings.

FIG. 12 is a partially sectional view of the hook component of FIG. 11 being pushed against the bending die of FIG. 11, to bend the hook component and adjust the contour of the hook component to fit a bone, in accordance with aspects of the present teachings.

FIG. 13 is a partially sectional view of the hook component of FIG. 12 received on a bone and defining a drilling path for a drill bit of a drill that is forming a hole in the bone between an aligned pair of apertures of the hook component, with an adjustable depth stop being used to limit the depth of the drill bit in the bone, in accordance with aspects of the present teachings.

FIG. 14 is a partially sectional view of the hook component and bone of FIG. 13 after placement of a bone screw through the bone and between the pair of apertures to secure the hook component to the bone, in accordance with aspects of the present teachings.

FIG. 17 is a view of a third embodiment of an exemplary bone plate for fixing a fractured rib bone, with components of the bone plate disposed in an exemplary assembled configuration in the absence of bone and fasteners, in accordance with aspects of the present teachings.

FIG. 18 is a view of a fourth embodiment of an exemplary bone plate for fixing a fractured rib bone, with components of the bone plate disposed in an exemplary assembled configuration and corresponding in structure to plate components of FIGS. 4-7, in accordance with aspects of the present teachings.

FIG. 19 is a view of a fifth embodiment of an exemplary bone plate for fixing a fractured rib bone, with the bone plate configured as a unitary version of the bone plate of FIGS. 4-7, in accordance with aspects of the present teachings.

FIG. 27 is an elevation view of a seventh embodiment of an exemplary bone plate for fixing rib bones with the bone plate secured to a rib bone via integral sutures, taken generally from outward of the rib bone, in accordance with aspects of the present teachings.

FIG. 28 is an elevation view of an eighth embodiment of an exemplary bone plate for fixing rib bones with the bone plate secured to a rib bone via suture material, taken generally from outward of the rib bone, in accordance with aspects of the present teachings.

DETAILED DESCRIPTION

The present teachings provide systems, including methods, apparatus, and kits, for fixing bones, such as rib bones, with bone plates. The bone plates may include one or more clip portions and/or an integral fastener mechanism, among others.

In some embodiments, each bone plate may include an exclusively unilateral arrangement of hook portions for placement of each hook portion onto a bone from the same side of the bone. The hook portions thus may be sized before placement onto bone (e.g., during their manufacture and/or preoperatively) in correspondence with an expected (e.g., average or representative) size (e.g., thickness) of target bones, for a more convenient and/or accurate fit onto bone. Accordingly, bone plates with hook portions of different predefined sizes may be provided in a kit, to allow selection of a suitable bone plate (e.g., intraoperatively) for a selected target bone from the kit.

In some embodiments, the bone plates may include an integral fastener mechanism that is connected to the bone plates before their placement onto bone (e.g., during their manufacture). The integral fastener mechanism may include a flexible connector (a tie mechanism), such as a cable tie (also termed a zip tie), a line (i.e., a suture material, thread, and/or cord, etc.), a strap, and/or the like. The integral fastener mechanism may allow a plate body of each bone plate to be secured to bone more readily and/or adjustably. In some embodiments, the fastener mechanism may be a separate component(s), such as a separate cable tie(s) that secures the bone plate to bone.

Overall, the systems of the present teachings may provide various advantages over other plate-based fixation systems. The advantages may include easier installation of bone plates; a better and/or more customized fit of bone plates on bones; faster, easier, more secure, and/or a more adjustable connection of bone plates to bones; less impingement of nerves and/or vessels; and/or improved or comparable fixation with shorter bone plates and/or fewer fasteners; among others.

These and other aspects of the present teachings are described below, including, among others, (I) overview of an exemplary fixation system, (II) bone plates, including (A) clip portions/hook portions, (B) spanning portions, (C) apertures, (D) body components, (E) fastener mechanisms, and (F) plate materials; (III) accessories and kits; (IV) methods of fixing bone; and (V) examples.

I. Overview of an Exemplary Fixation System

Figure 1:
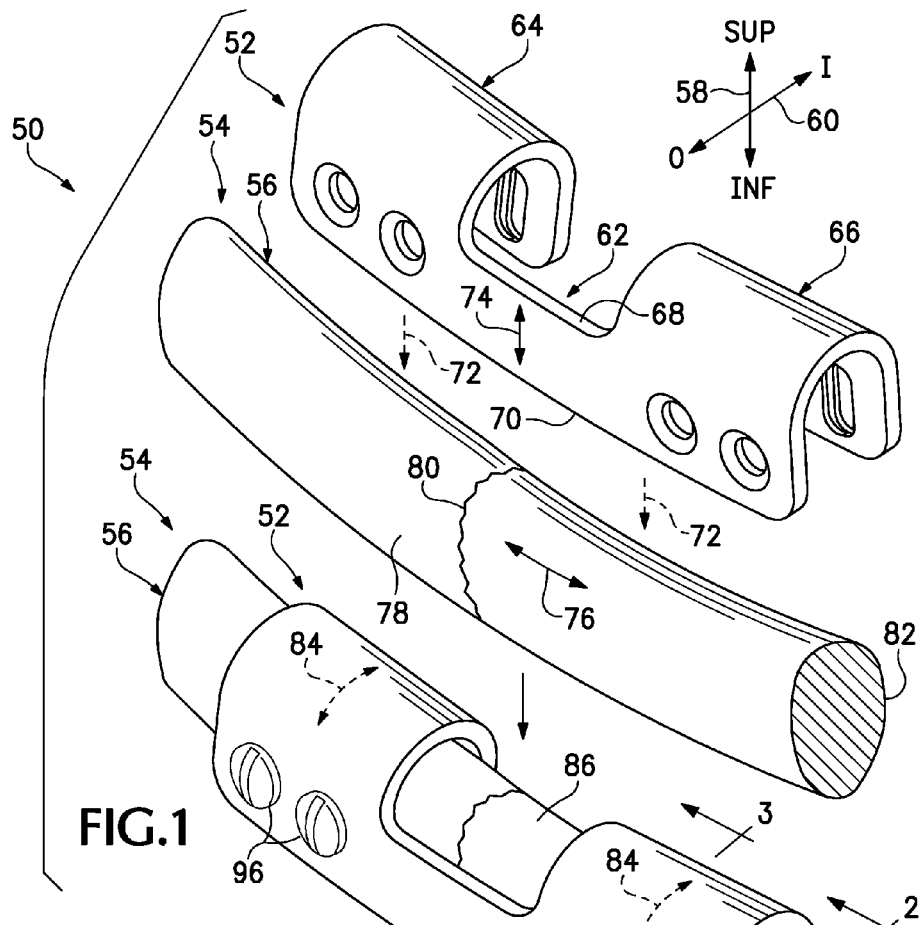
FIG. 1 is an exemplary flow diagram illustrating installation of an exemplary bone plate onto a fractured rib bone from a position superior to the rib bone, in accordance with aspects of the present teachings.

FIG. 1 shows an exemplary flow diagram 50 illustrating installation of an exemplary fixation system, including an exemplary bone plate 52, onto a target bone 54, here, a rib bone 56. For reference, anatomical axes 58, 60 are indicated. Superior-inferior axis 58 indicates relative superior ("SUP") and inferior ("INF") directions or positions in relation to rib bone 56. Outward-inward axis 60 indicates relative outward ("O") and inward ("I") directions or positions in relation to rib bone 56.

Bone plate 52 may be structured for placement onto rib bone 56 from a position superior to the rib bone. For example, the bone plate may include a spanning portion 62 and an exclusively unilateral arrangement of hook portions 64, 66 (also termed clip portions) extending from the spanning portion.

The unilateral (one-sided) arrangement of hook portions may be created by hook portions that each extend generally from only one (and the same one) of opposing edges 68, 70 of the spanning portion, namely, upper opposing edge 68. Accordingly, the unilateral arrangement of hook portions may create an open side of the bone plate, generally opposing the hook portions, to allow unobstructed translational placement of the bone plate onto a rib bone via superior to inferior translation motion, indicated at 72, of the bone plate. The translational motion may be generally parallel to a transverse axis 74 of the spanning portion that is orthogonal to a spanning axis or long axis of the bone plate. The spanning portion may be configured to be disposed axially on a rib bone (i.e., extending generally parallel to a long axis 76 of the rib bone), adjacent an outward surface 78 of the rib bone. The spanning portion may span a discontinuity or other structural weakness in the rib bone, such as a fracture 80. Furthermore, after the bone plate is installed, the hook portions may extend from the spanning portion at least partially around the rib bone, in the same general rotational direction, to positions adjacent an opposing inward surface 82 of the rib bone. The hook portions, due to their unilateral arrangement, may extend from the spanning portion exclusively via a superior path 84 over the rib bone (as opposed to an inferior path under the rib bone), adjacent a superior surface 86 of the rib bone.

The hook portions/clip portions may offer substantial advantages to the bone plate. For example, the hook portions may provide substantially better stabilization relative to a bone plate with narrow prongs and/or relative to a bone plate that does not extend to an opposing side of a bone (e.g., a bone plate without hooks). Accordingly, the bone plates described here may enable a bone to be fixed with a shorter bone plate secured with fewer fasteners. Alternatively, or in addition, the hook portions, due to their unilateral (e.g., superior rather than inferior) arrangement, may avoid impingement of nerves and vessels that may be located selectively on the one side of a bone (e.g., adjacent an inferior surface of the rib bone). Furthermore, the unilateral arrangement of hook portions may permit the hook portions to be preshaped (e.g., during manufacture) to fit onto rib bones of a particular size range, to provide a more customized fit for each plate recipient.

Figures 2, 3:
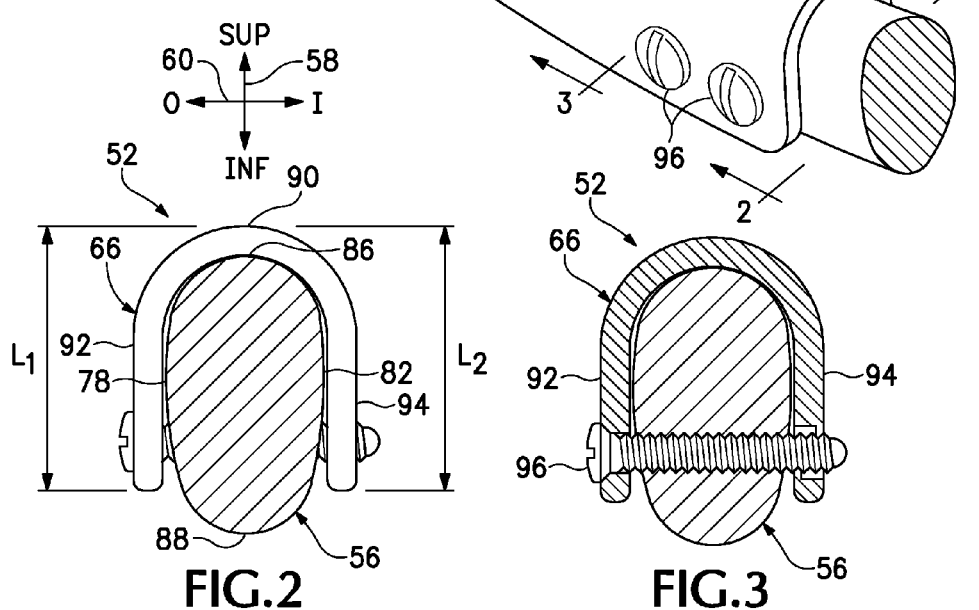
FIG. 2 is a partially sectional view of the rib bone and bone plate of FIG. 1 with the bone plate installed, taken generally along line 2-2 of FIG. 1.
FIG. 3 is a sectional view of the rib bone and bone plate of FIG. 1 with the bone plate installed, taken generally along line 3-3 of FIG. 1.

FIG. 2 shows an end view of bone plate 52 installed on rib bone 56. Hook portion/clip portion 66 may be disposed adjacent and/or may engage outward surface 78, superior surface 86, and inward surface 82 of the rib bone. Alternatively, or in addition, the hook portion may be disposed adjacent and/or may engage an inferior surface 88 of the rib bone (e.g., installed in an inverted orientation relative to what is shown here). The hook portion/clip portion may have a bridge region 90 disposed adjacent a superior region of the rib bone, and arms 92, 94 flanking and extending away from the bridge region. The arms may be of any suitable relative lengths, indicated as "L1" for arm 92 adjacent the spanning portion (the "proximal arm") and "L2" for arm 94 opposing the spanning portion (the "distal arm"), and may extend along any suitable portion of the width of the rib bone. Furthermore, the arms may have any suitable spacing, such as a spacing corresponding to the thickness of the rib bone. (The rib width, as used herein, is measured generally along the superior-inferior axis, and the rib thickness, as used herein, is measured generally along the outward-inward axis of the rib bone.) Further aspects of hook portions/clip portions that may be suitable are described elsewhere in the present teachings, for example, in Section II(A) and in Examples 1 and 11 below, among others. Further aspects of bone plates including clip portions are also described in U.S. patent application Ser. No. 10/927,824, which is incorporated herein by reference.

FIG. 3 show a sectional view of bone plate 52 installed on rib bone 56. The bone plate and/or hook portion 66 may be secured by any suitable fastener mechanism. For example, the bone plate and/or hook portion may be secured by bone screws 96 (see FIG. 1 also) received in openings of the bone plate and extending into the rib bone. In some examples, the bone screws (and/or other suitable fastener(s)) may extend through the rib bone, such as to lock to opposing arm 94 of hook portion 66. Accordingly, the fastener may have a length that corresponds to the arm-to-arm spacing of the hook portion. In some examples, the bone plate and/or hook portion may be secured by an integral fastener mechanism. Further aspects of fastener mechanisms that may be suitable for securing bone plates to bones are described elsewhere in the present teachings, for example, below in Section II(E) and in Examples 1, 10, and 11, among others. Further aspects of fasteners are also described in U.S. patent application Ser. No. 10/927,824, which is incorporated herein by reference.

II. Bone Plates

The bone plates may include one or more hook portions and a spanning portion that connects and spaces the hook portions (or the bone plates may have no hook portions). The hook portions of a bone plate may extend transversely from the spanning portion in any suitable arrangement, such as a unilateral (one-sided) configuration, i.e., in the same one of two opposing lateral directions from the spanning portion, or a bilateral (two-sided) configuration, i.e., in both opposing lateral directions from the spanning portion. Further aspects of the bone plates are described in the following sub-sections, including, among others, (A) hook portions, (B) spanning portions, (C) apertures, (D) body components, (E) fastener mechanisms, and (F) plate materials.

A. Clip Portions/Hook Portions

The bone plates each may include one or more hook portions (also termed clip portions). A hook portion, as used herein, is any region of a bone plate configured to be received by a bone so that the hook portion is disposed adjacent generally opposing surfaces of the bone. Accordingly, the hook portion may extend in a generally circumferential direction at least partially (or completely) around a bone, to wrap at least partially (or completely) around the bone. The hook portion may extend around any suitable portion of a bone's circumference, such as at least about one-half to three-fourths.

A hook portion may have any suitable contour or shape. For example, the hook portion may match, at least substantially, a surface contour of a bone for which the hook portion is configured. In some examples, the hook portion may be generally U-shaped, V-shaped, J-shaped, or O-shaped (e.g., circular, elliptical, oval, ovoid, etc.), among others, with a generally curved and/or angular contour. The hook portion thus may contact the bone along any suitable extent of the inner surface of the hook portion. The hook portion may have first and second regions (arms) configured to be disposed adjacent generally opposing bone surfaces, and a third region (a bridge region) disposed between and connecting the arms. In some examples, the hook portion may be included in a plate or plate component having a fourth region (the spanning portion) extending from the hook portion, such as from only one of the arms. In some examples, both arms (or only one arm) and the bridge region of the hook portion may contact the bone. In some examples, the bridge region may be spaced from the bone. The hook portion may be contoured before (e.g., during manufacture and/or preoperatively) and/or during installation according to the size and/or shape of a target bone (e.g., see Section IV).

A hook portion may be configured to be received on and to contact any suitable side(s) of a bone. The hook portion thus may be received from a superior, inferior, anterior, posterior, lateral, and/or medial direction, among others, onto the bone. The bridge region of the hook portion thus may be positioned adjacent a corresponding surface of the bone or may be rotated after the hook portion is received so the bridge region is positioned adjacent a different surface of the bone. Furthermore, the arms of the hook portion may be configured to be disposed adjacent any suitable generally opposing bone surfaces, such as surfaces that are posterior and anterior, inward and outward, medial and lateral, superior and inferior, or a combination thereof. In exemplary embodiments, for the purposes of illustration, the hook portion may be received from a superior direction onto a rib bone. The bridge region of the hook portion thus may be disposed adjacent and/or in engagement with a superior surface of the rib bone, and the arms of the hook portion thus may be disposed adjacent and/or in engagement with inward (internal) and outward (external) surfaces of the rib bone, generally anterior and posterior surfaces and/or medial and lateral surfaces. Two or more hook portions of a bone plate may have the same or different orientations on bone, to oppose and/or contact the same or different sides/surfaces of the bone.

A hook portion may have any suitable spacing, structure, and disposition of its arms. Generally the arms may be spaced about the same as the distance between generally opposing surfaces of a target bone, that is, about the width, thickness, and/or diameter of the bone where the hook portion will be disposed. However, in some examples, the arms may be spaced somewhat greater than this distance, at least when the hook portion is first placed on bone, to facilitate placement. Alternatively, the arms may be spaced somewhat less than this distance, so that the arms of the hook portion, particularly distal regions of the arms spaced from the bridge region, may be urged farther apart as the hook portion is placed onto bone. In some cases, the hook portion may have a bias to return to its original configuration, such that the arms, if urged apart by bone, tend to opposingly engage the bone due to the bias. The arms may be generally linear or may bend along their long axes. Furthermore, the arms may be nontwisted or may twist. The arms may be at least substantially parallel, or may diverge or converge toward their distal ends (spaced from the bridge region). In exemplary embodiments, the arms may have a spacing that corresponds to the thickness of a rib bone (e.g., see Example 11).

A hook portion may have any suitable width. The width of the hook portion may be measured between opposing edges of an arm and/or the bridge region, for example, generally parallel to the long axis of the bone when the hook portion is disposed on bone. The width may be substantially greater than the thickness of the bone plate (generally at least about twice or five times the thickness), so that the hook portion is plate-like rather than rod-like. Moreover, in some examples, the width of the hook portion may at least about as great as the width of the spanning portion, as measured across the bone plate for the spanning portion (see sub-section B below). The width of the hook portion may be generally constant within each arm and/or within the bridge region. Alternatively the width may vary within one or both arms, between the arms, within the bridge region, or between the arms and the bridge region. For example, the arms may taper away from the bridge region. Alternatively, or in addition, the bridge region may be narrower than the arms, to facilitate bending the bridge region (e.g., to facilitate adjustment of the spacing of the arms), or the arms may be narrower than the bridge region (e.g., to facilitate adjustment by bending the arms). In some embodiments, the hook portion may include one or more narrowed regions, at which the hook portion may be bent selectively, such as within one or both arms or the bridge region, and/or at a junction between an arm and the bridge region. Exemplary widths of the bridge region include about 2-50 mm or about 5-20 mm, among others.

A hook portion may have any suitable thickness. The thickness may be selected based on various considerations, such as reducing the profile of the hook portion on bone, providing a sufficient strength to fix bone, bendability, providing a sufficient thickness to form an offset lip or a thread in an aperture for engaging a fastener thread, and/or the like. Exemplary thicknesses include about 0.2-3 mm or about 0.5-2 mm, among others.

A hook portion may have any suitable number, shape, and arrangement of apertures. The hook portion may have no apertures or may define one or more apertures. Each aperture may be circular, square, elongate (such as oval, elliptical, rectangular, etc.), and/or the like. Each aperture may include or lack a counterbore. The apertures may be disposed in the arms and/or the bridge region of the hook portion. If two or more apertures are included in a hook portion, the apertures may be arrayed across the width and/or along the length of one or more arms and/or the bridge region, and/or may have a staggered disposition. In some examples, one or more pairs of apertures may be aligned, that is, configured to receive the same fastener with each aperture of the pair. Apertures of an aligned pair may be disposed in the arms and/or in the bridge region and one arm, among others. Each aligned pair of apertures may include zero, one, or two locking apertures. Apertures of an aligned pair may have the same general shape, such as oval or circular, or may have different shapes, such as oval and circular, among others. Furthermore, apertures of an aligned pair may be of generally the same size, such as about the same length and/or width, or may have different lengths and/or widths. In exemplary embodiments, apertures of an aligned pair may be have about the same length, with one of the apertures being narrower than the other to create retention structure to lock a fastener in position. Providing two or more aligned pairs of apertures in the hook portion may lead to enhanced torsional and/or bending stability of the fracture site, by restricting rotation of the hook portion relative to the bone. The thickness of the bone plate adjacent the aperture(s) (in the hook portion and/or other portions of the plate) may be generally the same as, less than, or greater than the thickness of the plate away from the aperture(s). Plate thinning near the apertures may provide a recess for reducing the profile of fasteners placed in the apertures, and plate thickening near the apertures may reinforce the aperture.

Each aperture may be locking or nonlocking. Locking apertures generally include a retention structure to engage a fastener, such as through a thread of the fastener, and restrict axial movement of the fastener in both axial directions. The retention structure may be one or more ridges formed by the wall of a locking aperture. The ridges may be generally helical, to form a thread, at least partially linear to form a locking slot, and/or the like. Further aspects of locking slots are described below (e.g., in Example 1) and in U.S. Provisional Patent Application Ser. No. 60/548,685, filed Feb. 26, 2004, which is incorporated herein by reference.

A hook portion (and/or spanning portion) may have any suitable surface structure. The surface structure may be formed by an inner surface, an outer surface, and/or a side(s)/edge(s)/end(s) disposed between the inner and outer surfaces. The surface structure may include one or more projections, such as a ridge(s) or bump(s), or one or more depressions, such as a groove(s) or dimple(s). If a projection, the projection may be relatively sharp and/or pointed or may be relatively dull and/or rounded, among others. Exemplary surface structure that may be suitable includes one or more prongs or sharp ridges to engage and/or penetrate bone (e.g., see Example 9), one or more projections to space the body of the hook portion from bone, one or more grooves or notches to receive and retain a suture (e.g., see Example 10), and/or the like.

B. Spanning Portions

The bone plates each may include one or more spanning portions. A spanning portion, as used herein, is any region of a bone plate configured to extend between (and optionally beyond) two or more hook portions of the bone plate, such that the hook portions are disposed in a spaced relation along the spanning portion (e.g., along the spanning and/or long axis of the bone plate). Accordingly, the spanning portion may extend in a generally axial direction along a bone, to span a discontinuity (such as a fracture) and/or structural weakness of the bone.

A spanning portion may have any suitable contour or shape. For example, the spanning portion may match, at least substantially, a surface contour of a bone for which the spanning portion is configured. For example, the spanning portion may be generally linear or bent as it extends between hook portions (along a spanning axis (e.g., a long axis) of the bone plate). If bent, the spanning portion may have a concave and/or convex bend along its inner surface, based, for example, on the surface contour of a bone for which the spanning portion is configured. The spanning portion also may be linear or curved transverse to the spanning axis, for example, across its width (and on its inner and/or outer surfaces), based, for example, on a local circumferential contour of the bone that is linear or curved, respectively. The spanning portion thus may be configured to contact the bone along any suitable extent of its inner surface. The spanning portion may be bent before and/or during installation according to the shape of bone or may be nonbent.

A spanning portion may be configured to be received on any suitable side/surface of a bone. The spanning portion thus may be disposed adjacent a superior, inferior, anterior, posterior, lateral, and/or medial bone surface, among others. In some examples, the spanning portion may be disposed adjacent substantially only one side/surface of a bone, such as a surface that is superior, inferior, outward (external), or inward (internal; e.g., an inward surface of a rib bone). In some examples, the spanning portion may be disposed adjacent and may contact two or more bone surfaces. The spanning portion thus may extend along bone from any suitable region(s) of each hook portion. Exemplary regions include only one arm, or one arm and the bridge region of a hook portion, among others. In any case, the spanning portion generally extends adjacent, and partially defines, an opening or gap that extends between a pair of hook portions, for example, an open region of the bone plate extending between the respective bridge regions and/or the respective distal (and/or proximal) arms of a pair of hook portions. The spanning portion also may extend beyond a hook portion, for example, beyond a proximal arm of a hook portion, to create an extension region of the spanning portion.

A spanning portion may have any suitable dimensions, such as length (L; measured along the spanning axis of the bone plate between the hook portions), width (W; measured across the spanning portion, transverse to the spanning axis), and thickness (T; measured between the inner and outer surfaces of the bone plate). Generally, $L \geq W > T$. However, in some examples, the length, as defined above, may be less than the width. For example, the hook portions may be disposed relatively close to one another (so that the spanning portion is relatively short) and/or the spanning portion may be relatively wide in relation to the spacing between the hook portions. Furthermore, the width of the spanning portion may be substantially greater than the thickness of the bone plate (generally at least about twice or five times the thickness), so that the spanning portion is plate-like rather than rod-like. The width may be generally constant or may vary as the spanning portion extends between the hook portions. In some embodiments, the spanning portion may include one or more narrowed regions (e.g., scallops; see Example 6) and/or thinned regions at which the spanning portion may be selectively bent. Exemplary widths of the spanning portion include about 2-30 mm or about 5-20 mm, among others. The thickness of the spanning portion may be about the same as, less than, or greater than the thickness of the hook portions. The thickness may be selected based on various considerations, such as reducing the profile of the spanning portion above bone, a sufficient strength to fix bone, bendability, and/or the like. The thickness may be constant or may vary, for example, at regions of overlap with another plate component and/or near apertures. Exemplary thicknesses of the spanning portion include about 0.2-3 mm or about 0.5-2 mm, among others.

A spanning portion may have any suitable number, shape, and arrangement of apertures. The spanning portion may have no apertures or may have one or more apertures. Each aperture may be circular, square, elongate (such as oval, elliptical, rectangular, etc.), and/or the like. Each aperture may include or lack a counterbore. The aperture may be locking or nonlocking, as described above for hook portions. If two or more apertures are included in a spanning portion, the apertures may be arrayed across the width and/or along the length, and/or may have a staggered disposition (e.g., see Example 10 below), among others. In some examples, one or more apertures of the spanning portion may be configured to be aligned with, and generally abut, corresponding apertures of a hook portion. Accordingly, the spanning portion may have one, two, or more apertures that align with one, two, or more apertures of a hook portion, to facilitate securing the spanning portion to the hook portion with a fastener(s) (e.g., in the absence of bone or via placement of the fastener(s) through the apertures and into bone). In some examples, the spanning portion may have a plurality of apertures configured to permit the hook portion to be aligned alternatively with different subsets (such as individual or pairwise members, among others) of the apertures. In some examples, the spanning portion may have apertures configured so that two or more hook portions can be secured to the spanning portion with fasteners at nonoverlapping positions of the spanning portion. These apertures may be arranged for securing the hook portions to opposing end regions of the spanning portion and/or to one or more intermediate regions of the spanning portion, among others.

C. Apertures

The bone plates may have apertures to perform any suitable functions. For instance, apertures may be configured to receive fasteners for securing plate components to each other and/or to a fractured bone. Alternatively, or in addition, apertures may be provided that are adapted to alter the local rigidity of the plates and/or to facilitate blood flow to the fracture to promote healing.

The apertures may have any suitable geometry(ies). For example, some apertures may be oblong (i.e., elongate, e.g., oval), whereas other apertures may be substantially circular. Oblong apertures may be used, for example, to permit flexibility in placement of a fastener in a range of translational and/or angular positions within the aperture. Furthermore, oblong apertures may permit a bone plate and/or plate component to slide parallel to the long axis of an oblong aperture, to facilitate adjustment of the plate and/or plate component position, after a fastener has been received in the aperture and in bone. Oblong apertures also may function as compression slots that bias a fastener toward or away from a discontinuity in the underlying bone. Circular apertures may be locking (such as threaded) or nonlocking apertures. Alternatively, or in addition, to engage a threaded fastener, the circular (or other) apertures may be configured such that a nut, clip, and/or other retaining device can engage an end or other portion of the fastener where it extends from the aperture. Furthermore, circular apertures may be used to receive other fasteners, such as pins, flexible connectors (such as lines (e.g., suture material, threads, cords, etc. that are monofilament or multi-filament in construction), straps, belts, flexible wires, etc.), and/or the like, after the bone plate is positioned on bone. The apertures may include counterbores that allow the head of fasteners to have a reduced profile above the bone plate and/or to lie substantially flush with the top surface of the plate.

The apertures of the bone plates may have various sizes, depending on their intended usage. For example, if used with fasteners, the apertures may be sized for different sized bone screws, such as bone screws with diameters of 2.1, 2.7, 3.5, and/or 4.0 mm. Generally, the larger the plate, the larger the number (and/or size) of apertures, so that larger plates may allow relatively larger numbers of screws (and/or larger screws) to be used. Thus, bone plates used to treat larger bones may include relatively larger apertures, or relatively larger numbers of apertures. Providing relatively greater numbers of apertures to accept bone fasteners may lead to relatively greater torsional and/or bending stability of the fracture site, when the bone plate is installed on a bone. The apertures in a particular plate may have a hybrid arrangement, such as a size of 3.5 mm in one region of the plate, and a size of 2.7 mm in another region of the plate, among others. In other examples, the apertures may be configured to receive flexible connectors. The apertures thus may be sized in close correspondence with the cross-sectional size of a flexible connector to be placed through the apertures. Alternatively, the apertures may be oversized (sized to be substantially wider, such as at least about twice as wide) relative to the flexible connector to facilitate threading the connector through the apertures.

In general, the apertures may have any suitable arrangement in the plate. For example, the apertures may be clustered together at end regions of the bone plate, to increase the number of fasteners that can be used to fix the associated segment(s) of bone(s) via the plate, or they may be spaced substantially evenly along the length of the plate, including regions of the plate that do not extend to an opposing side of a bone. The apertures may be positioned along a line, for example, with the apertures positioned along the length of the plate, or the apertures may be arranged in a two-dimensional pattern, increasing the density or effectiveness of fasteners that may be used.

D. Body Components

The bone plates may have any suitable number of plate body components to form the plate body (i.e., the entire bone plate or the plate-like portion(s)) of each bone plate. For example, the bone plates may be unitary (e.g., formed as a single monolithic structure by a single body component) or may have two or more pieces configured to be secured to one another and to bone with fasteners. In some embodiments, first and second body components of a bone plate may be supplemented by a third, fourth, or even higher number analogous body component, with each body component being discrete. The various body components of the bone plate may be used alone or in any suitable combination, as appropriate or desired for a given application. The various body components (e.g., a pair of hook components) also may be configured to have the same or different shapes and sizes.

The body components of a bone plate may be configured to be assembled in an overlapping configuration. The overlapping configuration may abut an inner surface region of one of the body components with an outer surface region of another of the body components. The regions of overlap of the body components may be geometrically similar to adjacent non-overlapping regions, or they may be specially configured to facilitate the overlap. For example, the thickness of one or both body components may be reduced in the regions of overlap. In some embodiments the overlapping regions may be beveled, and/or tapered, so that the boundary between the overlapping and nonoverlapping regions of a body component may be relatively smooth along the inner (bone-facing) and/or outer (non-bone-facing) surfaces of the bone plate. Alternatively, or in addition, surfaces of body components that contact one another may be configured and/or treated (e.g., roughened) to reduce slippage or the like. In some examples, a pair of body components may include a detent mechanism, such as complementary projections and cavities (e.g., pins received in holes) formed on mating surfaces of the pair of body components, to reduce slippage of the body components relative to one another.

E. Fastener Mechanisms

The bone plates may be secured to bone, and discrete body components (if any) of the bone plates connected to one another, using any suitable fasteners and at any suitable time. The fasteners generally comprise any fastener mechanism, including screws, bolts, nuts, pins, hooks, lines (e.g., suture material, cord, thread, etc.), straps, cable ties, and/or wires, among others. (In some cases, the fasteners may include adhesives and/or other nonmechanical mechanisms.)

Exemplary fasteners may be machine screws, to secure plate components (e.g., body components) to one another, and/or bone screws. Each bone screw may be received in bone and in a single aperture of the bone plate, a pair of aligned apertures disposed adjacent generally opposing bone surfaces (such as aligned apertures of a hook portion), and/or three or more aligned apertures provided by two or more plate components. The components may be connected to each other off of bone and/or on bone.

The bone screws may be unicortical, bicortical, and/or cancellous bone screws, among others. Unicortical and bicortical bone screws typically have relatively small threads for use in hard bone, such as near the middle of a clavicle, whereas cancellous bone screws typically have relatively larger threads for use in soft bone, such as in a rib. Unicortical bone screws penetrate the bone cortex once, adjacent a single surface of the bone. Bicortical bone screws penetrate the bone cortex at one surface of the bone, pass through the bone, and then penetrate the cortex again adjacent a generally opposing surface of the bone. Generally, unicortical screws provide less support than bicortical screws, because they penetrate less cortex.

The size and shape of the fasteners may be selected based on the size and shape of the apertures or vice versa. An exemplary fastener is a bone screw having features specifically adapted to fit the plate construction. For example, the bone screw may have a head wider than the width or diameter of an aperture defined by the bone plate, and a length approximating the spacing of the arms of a hook portion (and/or the thickness/diameter of a target bone). Alternatively, or in addition, the bone screw may have a thread configured to engage a lip or thread of an aperture of the bone plate.

Other exemplary fasteners include tie members. A tie member, as used herein, is any flexible connector that may be used to connect a bone plate (particularly a plate body of the bone plate) to bone and/or body components to one another. Exemplary tie members include lines (suture materials, threads, cords, etc.), straps, belts of cable tie mechanisms, and/or flexible wires, among others.

F. Plate Materials

The bone plates may be formed of any suitable material(s) of any suitable composition. Generally, the bone plates should be at least as stiff and strong as the section of bone spanned by the plates (typically, as stiff and strong as the bone in the absence of any discontinuity), yet flexible, bendable, and/or springy enough not to strain the bone significantly. In some examples, at least a hook portion(s) of the bone plate may be formed of a material with sufficient elasticity for the corresponding arms to spring back toward their original spacing after the arms have been urged apart (or pushed together) (e.g., see Section IV).

The bone plates, individual plate components, and/or integral (or separate) fasteners may be formed of biocompatible and/or bioresorbable material(s). Exemplary biocompatible materials that may be suitable include (1) metals (for example, titanium or titanium alloys, alloys with cobalt and chromium (cobalt-chrome), stainless steel, etc.); (2) plastics (for example, ultra-high molecular weight polyethylene (UH-MWPE), polymethylmethacrylate (PMMA), polytetrafluoroethylene (PTFE), polyetheretherketone (PEEK), and/or PMMA/polyhydroxyethylmethacrylate (PHEMA)); (3) ceramics (for example, alumina, beryllia, calcium phosphate, and/or zirconia, among others); (4) composites; (5) bioresorbable (bioabsorbable) materials or polymers (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, alginate, and/or chitosan), any copolymers thereof, etc.); (6) bone tissue (e.g., bone powder and/or bone fragments); and/or the like. In some examples, these materials may form the body of the bone plate and/or a coating thereon. The components of a bone plate may be formed of the same material(s) or different materials.

III. Accessories and Kits

The bone plates described herein may be used with various accessories and/or may be supplied in a kit. These accessories may be used, alone or from a kit, during the preparation, installation, and/or removal of bone plates (including the associated fasteners), among others. Exemplary accessories may include bone calipers, dies, hole-forming devices, drivers, and/or the like. Bone calipers may be used to measure the size of a bone to be fixed (e.g., see Example 2). Measurement of the size may facilitate selection of a suitable bone plate/plate component(s) (e.g., see Example 11), a suitable die for bending a bone plate/plate component(s) (e.g., see Examples 3 and 5), and/or suitable fasteners (such as by length, e.g., see Example 11) for securing the bone plate/plate component(s) to bone, among others. The die may permit a bone plate to be shaped pre- and/or intraoperatively, for example, by a surgeon installing the plate. Furthermore, the die may permit the bone plate to be shaped to conform at least substantially to a particular size or size range of fractured bone (or segment of a bone), such as a fractured rib. A hole-forming device such as a drill with an adjustable drill stop may be used to drill a hole in the bone to a desired depth, based, for example, on the measured size of the bone (e.g., see Example 4). A driver such as a screwdriver may be used to install and/or remove fasteners.

The bone plates, fasteners, accessories, etc. described above and elsewhere in the present teachings may be provided singly and/or as a kit, in combination with one another and/or yet other accessories. The kit may include, among others, a set of bone plates constructed to fit various sizes of bones and/or regions of bones (e.g., see Section IV and Example 11 below). For example, the kit may include plates configured to fit rib bones and/or clavicles of various sizes and shapes, and/or to fit on various regions of a rib bone and/or a clavicle, among others. In addition, the kit may include fasteners of one size or of various sizes that correspond to different sizes of bone plates (e.g., see Example 11). Moreover, the kit may include instrumentation for measuring one or more dimensions of the bone, and/or for intraoperatively bending and installing a bone plate (or portion thereof). For example, the instrumentation may include bone calipers, an adjustable bending die, and/or a drill bit including a depth stop. The kit also may include a case or organizer, instructions, drivers such as screwdrivers for installing and/or removing mounting hardware, and/or other accessories related to bone plates.

Further aspects of accessories and kits are described elsewhere in the present teachings, for example, below in Examples 2-5 and 11, among others.

IV. Methods of Fixing Bone

This section describes exemplary method steps that may be suitable to fix bones with the bone plates of the present teachings. These steps and those described elsewhere in the present teachings may be performed in any suitable order, in any suitable combination, and any suitable number of times.

A bone to be fixed may be selected. Exemplary bones may include rib bones and/or clavicles. Other exemplary bones may include bones of the arms (radius, ulna, humerus), legs (femur, tibia, fibula, patella), hands/wrists (e.g., phalanges, metacarpals, and carpals), feet/ankles (e.g., phalanges, metatarsals, and tarsals), vertebrae, scapulas, pelvic bones, and/or cranial bones, among others. The bone may be selected from any suitable species, including human, equine, canine, and/or feline species, among others. The bone may lack or include a discontinuity or other structural weakness, which may have been produced developmentally (e.g., as a result of a genetic mutation) and/or as a result of trauma, disease, and/or surgical intervention. Accordingly, exemplary discontinuities for use with the bone plates described herein may include joints, fractures (breaks in bones), osteotomies (cuts in bones), and/or nonunions, among others.

A discontinuity in the bone may be reduced. For example, a fractured bone may be set. Reduction of the discontinuity may be performed before, during, and/or after a bone plate is secured to the bone.

An aspect of the bone may be measured, generally in the vicinity of the discontinuity. Measurement may be performed with any suitable measuring device or method, such as calipers, a ruler, a tape measure, a fluoroscope (e.g., by fluorography), and/or the like, or may be performed as a visual estimate. The aspect may correspond to a characteristic dimension (such as thickness, width, length, and/or diameter, among others). Alternatively, or in addition, the aspect may correspond to a curvature or surface contour of the bone, among others.

A bone plate may be selected for installation on the bone. The bone plate may be selected from a set of available bone plates. For example, the set may include bone plates with different arm-to-arm spacings (also termed leg-to-leg spacings) and/or radii of curvature for their hook portions, and/or different lengths of spanning portions, among others. Selection may be performed based on the type, size, and/or contour of the bone, among others, and thus may be based on a measured, average, and/or expected aspect (such as thickness) of the bone. The bone plate may be manufactured with a predefined size and shape and/or may be custom contoured for a particular bone, bone region, and/or for the particular anatomy of the patient. Custom contouring (generally, bending) may be performed pre- and/or intraoperatively by hand, with a bending tool, and/or with a die, among others. Further aspects of bone plates with hook portions of different sizes are described elsewhere in the present teachings, for example, below in Example 11.

The bone plate selected may be positioned on bone. The step of positioning may include placing a unitary bone plate (or unitary plate body) or two or more plate components on the bone, from any suitable direction. In exemplary embodiments, the bone plate and/or a plate component(s) may be placed on a bone from above the bone (from a superior direction). With two or more plate components, the plate components may be placed on bone in any suitable order. In some embodiments, a first plate component including a first hook portion and a spanning portion may be placed onto bone, and then a second plate component including a second hook portion may be placed onto bone, overlapping and outside of the spanning portion. In some embodiments, this order and/or disposition of placement may be reversed. Furthermore, additional plate components also may be placed on the bone. In some examples, a hook portion of the bone plate may have an arm-to-arm spacing that is less than the thickness/width/diameter of the bone, so the arms of the hook portion are urged apart as the bone plate is placed onto the bone.

In some examples, the hook portions may have an inherent elasticity that promotes placement and/or retention of the hook portions. In particular, the arms of a hook portion may be biased toward their original spacing, such that the arms grip bone if they are urged apart by bone. For example, the arms may converge as they extend from a bridge region of the hook portion, and the bone may taper in the direction of hook portion placement (e.g., see FIG. 14). Accordingly, the end regions of the arms may be urged apart as they pass over a thicker/wider region of the bone, and then may spring back toward one another (toward their original converged disposition) as the hook portion is advanced farther onto the bone, which may provisionally (or more permanently) retain the hook portion on the bone.

The selection and/or positioning of bone plates, as described in the present teachings, may take advantage of the differential characteristics, accessibility, and/or sensitivity of different portions or surfaces of a given bone. For example, a bone plate with hook and spanning portions may be selected and positioned such that the spanning portion and/or hook portion (or a region(s) thereof, such as an arm and/or bridge region) is located along a more accessible and/or less vascularized or innervated portion of the bone, such as the outward or anterior surface of a rib bone. In this way, relatively more bone plate is positioned adjacent more accessible and/or less sensitive portions of the bone, and relatively less bone plate is positioned adjacent less accessible and/or more sensitive portions of the bone. In some embodiments, the bone plate may be positioned on a rib bone such that no hook portion of the bone plate extends adjacent a neurovascular bundle disposed on an inferior side of the rib bone.

One or more holes may be formed in the bone. The holes may be formed with a hole-forming device, such as a drill, a punch, and/or a self-drilling bone screw, among others. If formed with a drill, a drill stop, such as the drill stop of Example 4, may be used to prevent forming a hole that is too deep, which may cause unnecessary tissue damage and/or remove bone unnecessarily. The holes may be formed before or after one or more plate components are positioned on the bone. If formed after a plate component is positioned on the bone, the hole may be formed in alignment with one aperture, or two, three, or more aligned apertures of one plate component, or two or more overlapping plate components. Accordingly, the aperture(s) may function, at least partially, as a guide for the hole-forming tool. However, a guide wire and/or cannula also or alternatively may be used to guide the hole-forming tool. The holes may extend from an aperture into bone and/or through bone. In some examples, a hole may extend between a pair of aligned, spaced apertures of a hook portion. Further examples of holes formed in bone are described elsewhere in the present teachings, for example, below in Example 9, among others.

The bone plate may be secured to the bone with one or more fasteners, such as bone screws and/or a tie mechanism(s), among others. One or more fasteners thus may be selected. The fasteners may be selected, for example, to have a diameter less than the width/diameter of a target aperture, and, if threaded, to have a thread configuration corresponding to the size/offset of an aperture lip (for an elongate locking aperture) or to the pitch of an aperture thread (for a circular locking aperture). The fasteners also or alternatively may be selected to have a length (particularly a shaft length for a bone screw) about the same as the measured or expected thickness/width/diameter of the bone. The fasteners may be placed through apertures and into pre-formed holes or may form holes themselves. The fasteners may engage a plate component adjacent one side of the bone and/or adjacent generally opposing surfaces of the bone, among others. Each fastener may extend through a single plate component or two or more overlapping plate components. Accordingly, the fastener may secure two or more plate components together and/or to bone. In some examples, the fastener may lock to one or more plate components, adjacent only one side of the bone or adjacent each of two generally opposing surfaces of the bone. In some examples, the fastener may be tightened until generally opposing regions of a plate component or bone plate are compressed against the bone. The fasteners may be placed into apertures of the bone plate in any suitable order. For example, a first plate component may be partially or completely secured to the bone first, and then a second plate component secured to the bone, or the plate components may be secured to bone at least initially with the same fastener(s). The fasteners may be installed and/or removed by hand and/or with the assistance of a suitable driver, such as a screwdriver.

V. Examples

The following examples describe selected aspects and embodiments of the present teachings, including exemplary fixation systems, bone plates, configurations for assembly of bone plates from plate components, and fastener mechanisms, among others. These examples and the various features and aspects thereof are included for illustration and are not intended to define or limit the entire scope of the present teachings.

Example 1

Bone Plate with Multiple Plate Components

This example describes an exemplary bone plate 120 for fixing rib bones and including a plurality of plate components that are connected to one another via fasteners; see FIGS. 4-9.

FIG. 4 shows bone plate 120 fixing a fractured rib bone 122. Bone plate 120 may include one or more hook portions 124, 126 received on the bone and wrapping at least partially around the bone. For example, in the present illustration, the hook portions have been received from the superior side of (from above) the rib bone to oppose superior surface 128 and generally opposing surfaces 130, 132 (such as anterior and posterior, outward and inward, and/or medial and lateral surfaces, among others) of the rib bone. Each hook portion thus may include a pair of generally opposing arms 134, 136 extending from and connected by a bridge region 138 (see FIG. 5). Plate 120 also may include a spanning portion 140 extending generally axially along the bone and spanning a fracture 142 in the bone (see FIG. 4). The spanning portion may extend between the hook portions, to connect the hook portions.

Bone plate 120 may be secured to bone 122 using suitable fasteners, such as bone screws 144. The bone plate thus may define one or more apertures 146 for receiving the bone screws. The apertures may be disposed so that the bone plate can be secured with bone screws to bone fragments 148, 150 created by fracture 142 and disposed on opposing sides of the fracture.

FIG. 5 shows bone plate 120 before assembly, and FIGS. 6 and 7 show bone plate 120 after assembly into different configurations. The bone plate may be unitary or may include two or more plate components (body components) 152, 154 configured to be secured to one another and to bone. In some examples, each plate component may include a hook portion, and one or more plate components may include a spanning portion. A spanning portion may be connected to a hook portion unitarily in a plate component, as shown for component 152. Alternatively, or in addition, a spanning portion in a first plate component may be connected to a hook portion in a second plate component with a fastener mechanism. For example, the plate components may be configured to be placed into an overlapped configuration, shown at 156 in FIG. 6, so that an outer surface 158 of component 152 overlaps and abuts an inner surface 160 of component 154 (see FIG. 5). Alternatively, as shown in FIG. 7, or in addition, the plate components may be overlapped so that an inner surface of component 152 overlaps and abuts an outer surface of component 154. Accordingly, a distal end or overlapping region 162 of the spanning portion may be interposed between a hook portion and bone (see FIG. 6), or may be spaced from bone by the hook portion (see FIG. 7). The placement shown in FIG. 7 may space the inner surface of the spanning portion from the underlying bone and thus may be used, for example, in situations where it is desirable to leave a small gap between the bone plate and the bone in the vicinity of a fracture. This may promote a relatively greater blood supply to the bone near the fracture, possibly leading to faster healing in some cases.

Each of the plate components may include one or more apertures configured to be aligned with, and generally abut, a corresponding aperture of the other component, such as abutted aperture pair 164, 166 (see FIGS. 5 and 6). In some examples, the bone plates may have at least two pairs of abutted apertures provided by overlapping plate components, which may secure the plate components to one another more effectively. In some examples, two or more alternative alignments of abutted apertures may be permitted, so that the spacing between hook portions can be selected from two or more possible spacings (see Example 6).

Each hook portion may include one or more pairs of aligned apertures configured to be disposed adjacent generally opposing surfaces of a bone. For example, spaced aperture pair 168, 170 (see FIG. 5) may be configured to receive a bone screw 172 that extends through bone between apertures of the aperture pair (see FIGS. 4 and 8A). In some examples, the hook portion may include at least two spaced pairs of apertures, to secure the hook portion to bone more effectively and thus provide better stabilization of bone. Alternatively, the fastener may extend through a single aperture or an abutted aperture pair into bone, but not completely through the bone. In any case, one or more of the apertures may be a locking aperture, that is, an aperture configured to engage the fastener so that axial movement of the fastener in both axial directions is restricted.

In the present illustration, distal aperture 170 is an elongate locking aperture (a locking slot) having an offset lip with offset ridges 174, 176 (an offset lip) formed by opposing walls of this elongate aperture (see FIG. 8A). The ridges may be at least partially linear, extending parallel to the long axis of the aperture. Ridges 174, 176 may be configured to be received between adjacent (or nonadjacent) thread segments 178 of a thread 180 formed on the shaft of bone screw 172, so that engagement between ridges 174, 176 (or one ridge) and the thread segments locks the bone screw to the plate. Furthermore, rotation of the bone screw after the head of the bone screw has engaged the plate may urge the arms of hook portion toward each other, because the shaft of the screw can advance relative to locking aperture 170, whereas the head of the screw cannot advance relative to proximal aperture 168. Accordingly, this rotation may adjust the spacing of the arms and/or compression of the bone by the hook portion.

FIG. 8B shows another example of an elongate locking aperture 182 receiving a bone screw. In this example, only one of two opposing walls of the locking aperture has a ridge 184 configured to be received between thread segments of the bone screw.

FIG. 9 shows a portion of the bone plate including locking aperture 170. The locking aperture may be formed from an oval aperture flanked by recessed and/or thinned regions 186, 188 of the plate formed on respective inner and outer surfaces 190, 192 of the plate, and with opposing walls 194, 196 of the aperture. Alternatively, only one of the surfaces may be recessed, to form only one ridge or lip region to be received between thread segments (see FIG. 8B). Locking apertures, and particularly an aligned, spaced pair of apertures that include a locking feature, may secure the plate to the bone more effectively than a nonlocking aperture or aperture pair and thus may provide better fixation of the bone. Further aspects of locking apertures, particularly elongate locking apertures, are described in U.S. Provisional Patent Application Ser. No. 60/548,685, filed Feb. 26, 2004, which is incorporated herein by reference.

Example 2

Bone Caliper for Rib Measurement

This example describes an exemplary bone caliper 210 and methods of using the bone caliper to measure a rib bone to be fixed; see FIG. 10.

The bone plates optionally may be used with any suitable measuring devices, such as bone calipers, to measure one or more dimensions of a bone to be fixed. For example, FIG. 10 shows caliper 210 being used to measure the thickness of a rib bone 212. Caliper 210 may include an arcuate end portion 214, which is configured to conform to a preselected (e.g., superior) surface of the rib bone, and which also may be configured to wrap partially around another (e.g., posterior) surface of the bone. More generally, end portion 214 (and other portions) of the caliper may be adapted to conform to the size and/or shape of any desired bone(s), so that a similar instrument may be used to measure the thickness (and/or width/diameter) of various bones other than ribs. Caliper 210 also may include a clamping member 216, which may be attached to a movable measurement scale 218. Once end portion 214 of the caliper has been placed adjacent the bone being measured, scale 218 may be moved until member 216 makes contact with the bone. Then, as indicated at 220, the approximate thickness of the bone may be read from the scale.

The dimensions of a fractured bone, measured as above, or otherwise known, may be used for any suitable purpose. For example, the dimensions may be used to select an appropriate bone plate or plate component from a set of plates or components, and/or they may be used to pre- or intraoperatively shape a bone plate to fit the bone.

Example 3

Bending Die I

This example describes an exemplary bending die and methods of using the bending die to bend bone plates of the bone fixation systems of the present teachings; see FIGS. 11 and 12.

The bone plates optionally may be used with any suitable dies and/or hole-forming tools. The dies may be configured to bend the plates from a planar configuration and/or to adjust the shape of the plates from a bent configuration. The hole-forming tools may be used to form holes in bone and/or in bone plates, generally to facilitate placement of fasteners.

FIGS. 11 and 12 show an exemplary bending die 230 being used to shape a bone plate 232, or a component thereof, to fit a rib bone. In FIG. 11, the die has received the plate in a partially bent configuration, and in FIG. 12, the die is being bent with application of a compressive force through compression members 234, 236.

Die 230 may have a size and shape that approximates one or more cross sectional dimensions of a rib bone, to facilitate contouring a bone plate/plate component to match these dimensions at least substantially. In particular, the die may facilitate contouring plate component 232 to match the size (e.g., thickness) of the bone, and to match the shape and/or curvature of a preselected (e.g., superior) surface of the bone, for example, to reproduce at least part of the ovoid cross-sectional shape of a typical rib bone. To contour a bone plate, or a component thereof, using the bending die, a flat or partially contoured plate may be shaped around the die manually. Alternatively, or in addition, a tool such as pliers or another clamping mechanism may be used to add precision and/or mechanical advantage during bending. In some embodiments, the die may be narrower and tapered more than the actual shape of the bone, so that bone plates shaped by the die may be configured to compress the bone slightly even before being fixed into position on the bone. Die 230 may be configured to approximate the size and shape of a rib bone; however, more generally, dies may be provided that facilitate contouring of plates to match the dimensions of other bones, such as clavicles, among others.

Example 4

Drill System

This example describes an exemplary system for forming holes and placing fasteners for the bone fixation systems of the present teachings; see FIGS. 13 and 14.

FIGS. 13 and 14 show the use of a drill, drill stop, and fastener for mounting a bone plate to a bone.

FIG. 13 shows a drill 240 including a drill bit 242 drilling through a bone 244. Bit 242 has been guided into bone through an aperture 246 of bone plate 232, while the bone plate is in position on the bone. The drill bit may include an elongate shaft 248, and a drilling tip 250 attached to the shaft. An adjustable depth stop 252 may be disposed and secured along the drill bit at a selected axial position of the bit, so that a suitable length of the drilling tip extends beyond the depth stop. Securing the depth stop to the bit in this manner prevents the bit from penetrating the bone beyond a desired depth, and may reduce damage to tissue behind the bone, when the bone is drilled. Depth stop 252 may be secured to the bit by any suitable mechanism, such as a set screw 254, and/or engagement with grooves or slots provided along the length of shaft 248. The shaft of the drill bit may be provided with a scale, generally indicated at 256, for positioning the depth stop at predefined distances from the distal tip of the drill bit. Alternatively, or in addition, the depth stop may be positioned by measuring a desired distance from the distal tip with any standard measuring device, such as a ruler, tape measure, or caliper, among others.

FIG. 14 shows bone plate 232 attached to bone 244 with a threaded bone screw 260, in the hole formed by the drill bit (see FIG. 13). Screw 260 may be selected based on the measured thickness of the bone. In particular, a threaded screw may be chosen that is long enough to reach and engage a locking aperture 262 adjacent an opposing surface 264 of the bone, but not so long that a distal end 266 of the screw protrudes, or protrudes excessively, through the bone plate. This configuration may allow the screw to engage the plate securely and compress the plate and the underlying bone, while reducing or eliminating unnecessary physiological damage or discomfort to the patient.

Example 5

Bending Die II

Figure 15:
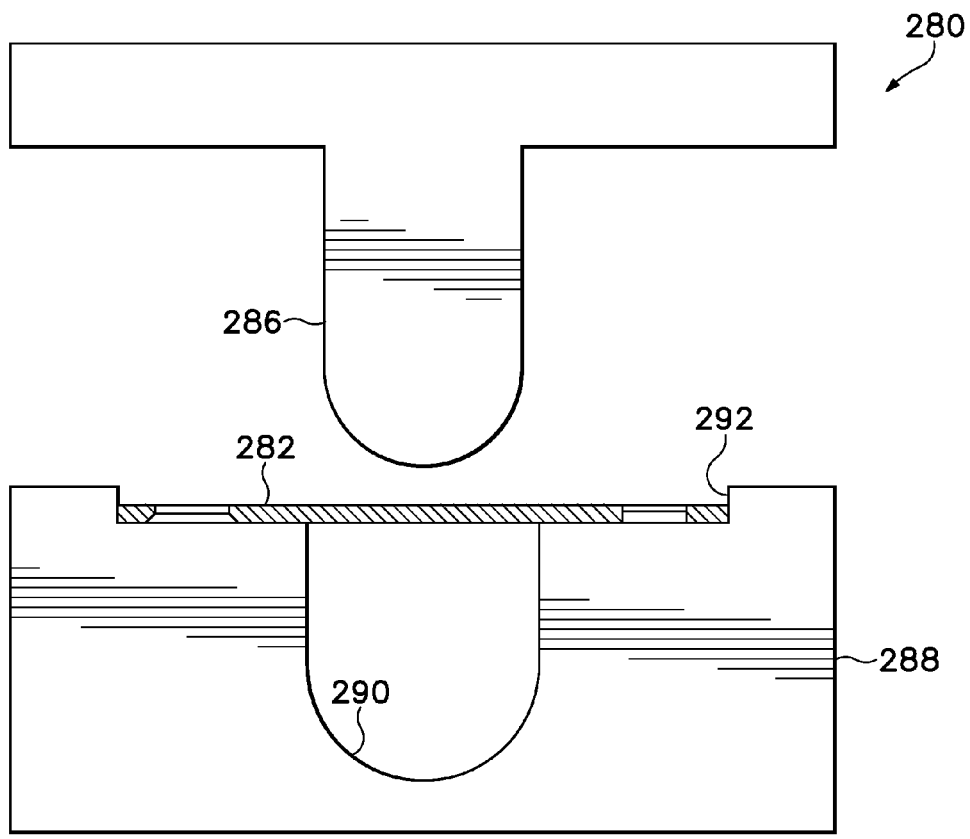
FIG. 15 is a partially sectional view of a die assembly holding a plate member before the plate member is bent into a hook component, in accordance with aspects of the present teachings.
Figure 16:
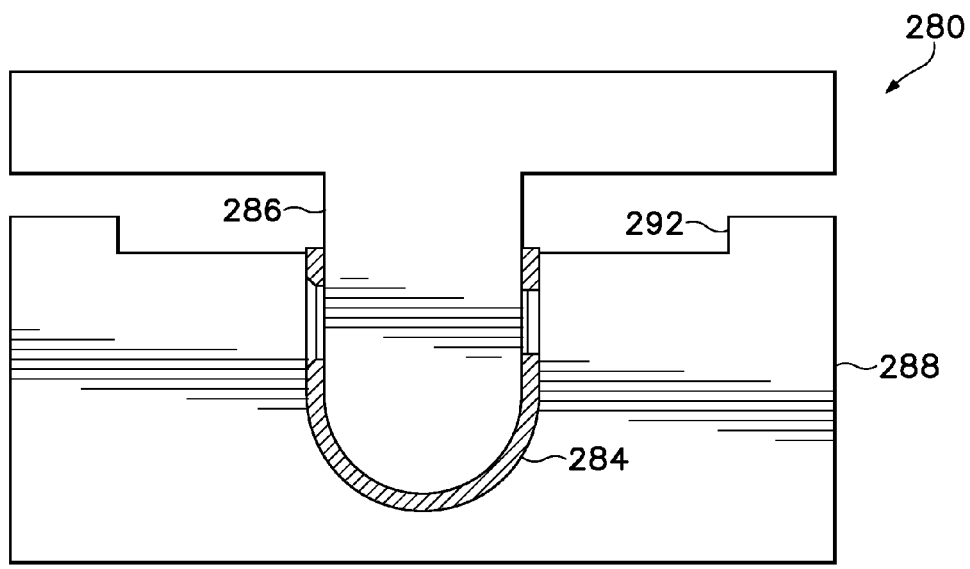
FIG. 16 is a partially sectional view of the die assembly and plate member of FIG. 15 after the die assembly has been used to bend the plate member into a hook component, in accordance with aspects of the present teachings.

This example describes another exemplary bending die and methods of using the bending die to bend bone plates of the rib fixation systems of the present teachings; see FIGS. 15 and 16.

FIGS. 15 and 16 show an exemplary die assembly 280 before (FIG. 15) and after (FIG. 16) bending a plate member 282 into a hook portion 284. The die assembly may include an anvil 286 configured to fit into a receiver 288, with a gap sufficient to accommodate the plate member disposed between the anvil and the receiver. The anvil may be configured to be pressed into the receiver, such as with a clamp device or one or more blows from a hammer, among others. The receiver may be configured to position the plate member over a cavity 290 of the receiver. For example, the receiver may include a recessed structure 292, projections, or the like, to restrict lateral movement of the plate member before and/or during bending.

A bending die and/or die assembly may be adjustable and/or available as part of a set to accommodate bones of different sizes and shapes. Thus, while the exemplary dies described above may have fixed dimensions, in some embodiments these dies may be internally adjustable, for example, using one or more internal set screws, such that the overall size and/or shape of the die may be set by adjusting the set screws. Alternatively, a plurality of bending dies, fixed and/or adjustable, may be provided for each size, shape, and/or type of bone, so that bone plate components may be shaped to any desired size. The range of sizes of the dies provided may correspond to an expected range in sizes of the type of bone being treated. For example, for contouring bone plates suitable for rib bones, dies may be provided that have maximum widths ranging between approximately 0.10 inches (about 2.5 mm) and approximately 0.50 inches (about 13 mm), or between approximately 0.15 inches (about 3.8 mm) and approximately 0.38 inches (about 10 mm), among others.

Example 6

Bone Plates with a Multi-Aperture Spanning Portion

This example describes exemplary bone plates having a spanning portion with a plurality of apertures; see FIG. 17. The apertures may be arranged so that a hook component can be assembled with and secured to a spanning portion at two or more positions along the spanning portion.

FIG. 17 shows an exemplary bone plate 310 for fixing a fractured rib bone. The bone plate may include a spanning component 312 having a spanning portion 314 and a first hook portion 316 formed unitarily with one another. The bone plate also may include one or more additional hook portions, such as hook components 318, 320 formed as separate components.

Spanning portion 314 may include a plurality of spanning apertures 322 arrayed along the length of this portion. Spanning apertures 322, and particularly subsets of these apertures, may be configured to be aligned with one or more hook apertures 324 of each hook portion. In the present illustration, adjacent pairs of the spanning apertures may be aligned with and abutted to adjacent pairs of hook apertures, shown at 326. Accordingly, each hook portion may be disposed at a plurality of selected positions along the spanning portion.

The apertures of the spanning portion may have any suitable spacing. The apertures may have a uniform spacing, as shown here, or may have an unequal spacing. For example, the apertures may be configured as groups (such as pairs, triplets, etc.) with unequal spacing between the groups, so that a hook component, with a corresponding number of apertures as each group, may be secured in alignment with a selected group. Alternatively, an unequal spacing may be suitable if each hook portion uses only one aperture assembly with the spanning portion.

In use, spanning component 312 may be positioned on a fractured rib, and one or more hook components 318, 320 may be positioned in alignment with apertures of the spanning portion. For example, the hook components may be positioned so that pairs of hook portions flank fractured regions of the rib. Accordingly, more severely fractured ribs may use a greater number of hook components in combination with the spanning component. In some examples, the spanning portion may be cut to a suitable length according to the length of bone or bone region to be spanned by the bone plate. Accordingly, a greater or lesser length of the spanning portion (or none) may be removed based on a lesser or greater number, respectively, of hook components to be used and/or a shorter or longer region, respectively, of bone to be fixed. Spanning portion 314 may be cut before or after spanning component 312 is positioned on and/or secured to bone. Furthermore, the spanning portion may define narrowed regions, such as scallops 328, at which the spanning portion may be bent selectively. Bending the spanning portion may be suitable to, for example, conform the spanning portion to an axial curvature of the rib.

Alternative configurations may be suitable. In some embodiments, the spanning component may be selected from a set of spanning components with different lengths of spanning portions and/or different numbers/spacings of apertures. In some embodiments, the spanning portion may be formed of a selectable number of modules, to adjust the length of the spanning portion, and/or the spanning portion may be a separate module (or a set of separate modules of various lengths) that can be selected for assembly with hook components.

Example 7

Bone Plate with Array of Plate Components

This example describes an exemplary bone plate 340 that may be assembled as an array of plate components; see FIG. 18.

FIG. 18 shows bone plate 340 including a tandem array of spanning components 342, 344 that overlap and can be secured to one another with fasteners received in aligned apertures, shown at 346. Each spanning component may include a hook portion and a spanning portion. Any suitable number of spanning components, of similar or distinct configuration, may be arrayed. One or more hook components may be secured to a spanning component (exactly one is shown here), or the bone plate may lack a distinct hook component.

Example 8

Bone Plate of Unitary Construction

This example describes an exemplary bone plate 360 having a unitary construction; see FIG. 19.

FIG. 19 shows bone plate 360 for fixing a fractured rib. Bone plate 360 may be formed as one component, so that a spanning portion 362 is joined to, and flanked by, hook portions 364, 366.

Example 9

Exemplary Fastener Mechanisms for Bone Fixation Systems

This example describes bone fixation systems that include various exemplary fastener mechanisms that may be suitable for securing the bone plates of the present teachings to any suitable bones, such as rib bones; see FIGS. 20-24. Each of FIGS. 20-24 is a cross-sectional view of a respective fixation system secured to a rib bone.

Figure 20:
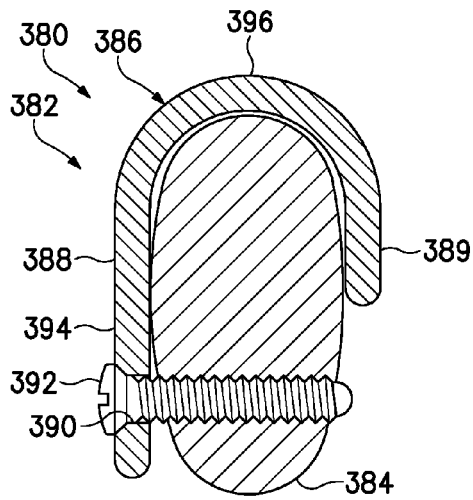
FIG. 20 is a sectional view of an exemplary system for fixing rib bones, taken generally through a hook portion of a bone plate of the system secured to a rib bone with a bone screw, in accordance with aspects of the present teachings.

FIG. 20 shows an exemplary system 380 for fixing rib bones. Fixation system 380 may include a bone plate 382 disposed on a rib bone 384 and having one or more hook portions 386 hooked onto the rib bone. Each hook portion may include arms 388, 389 of unequal (or approximately equal) length to produce a J-shaped (or U-shaped) hook portion. For example, proximal arm 388 may be longer than distal arm 389 (or vice versa). The proximal arm may define one or more apertures 390 for receiving a fastener, such as a bone screw 392. Aperture 390 may be positioned in a lower or more spaced region 394 of the proximal arm (relative to a bridge region 396 connecting the arms), for which there is no counterpart region on the distal arm. Accordingly, bone screw 392 may extend into the rib bone from aperture 390 without being received by the distal arm. The bone screw may extend only into the rib bone or through the rib bone. In some embodiments, the bone screw also may be received by the distal arm, in a locking configuration (e.g., see FIG. 3) or in a nonlocking configuration.

Figure 21:
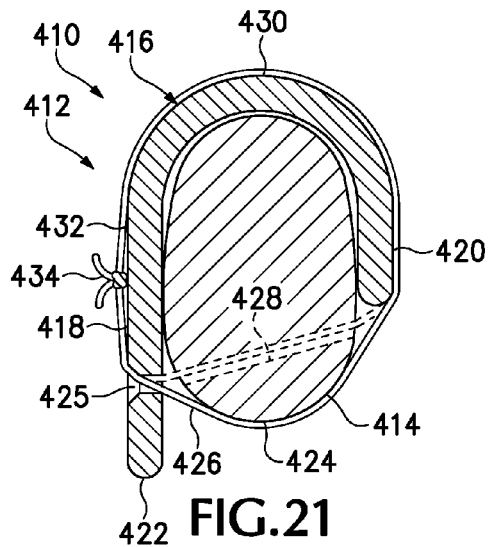
FIG. 21 is a sectional view of another exemplary system for fixing rib bones, taken generally through a hook portion of a bone plate of the system secured to a rib bone with a suture, in accordance with aspects of the present teachings.

FIG. 21 shows another exemplary system 410 for fixing rib bones. Fixation system 410 may include a bone plate 412 disposed on a rib bone 414 and having one or more hook portions 416 hooked onto the rib bone. Each hook portion may include arms 418, 420 of unequal (or approximately equal) length to produce or J-shaped (or U-shaped) hook portion. At least one of the arms may be of sufficient length to extend beyond the rib bone. For example, here, proximal arm 418 is longer than the width of the rib bone, such that end 422 is disposed inferior to local inferior nadir 424 of the rib bone. Proximal arm 418 (and/or distal arm 420) may define an aperture 425 for receiving a suture 426. The suture may extend at least partially or completely around the rib bone and/or at least partially through the rib bone, e.g., through a hole formed in the bone (indicated at 428 in phantom outline). Furthermore, the suture may extend over/around most (or all) of the hook portion, such as extending over distal arm 420, bridge region 430, and a major proximal portion 432 of proximal arm 418. Suture 426 may be secured by a knot 434 or by a suture retainer formed by the bone plate or as a distinct component. The bone plate may be secured exclusively by one or more sutures or by a combination of at least one suture and another type of fastener mechanism.

Figure 22:
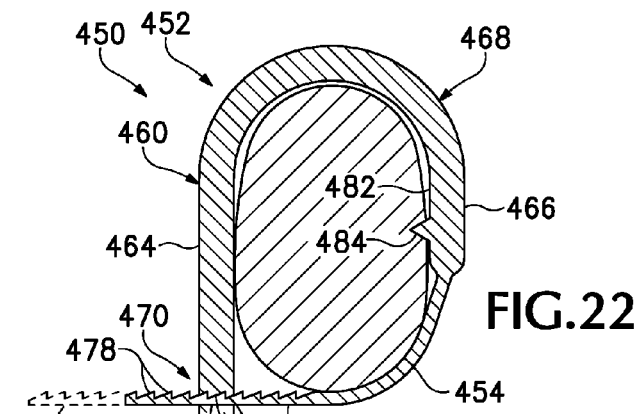
FIG. 22 is a sectional view of yet another exemplary system for fixing rib bones, taken generally through a hook portion of a bone plate of the system secured to a rib bone with an integral tie mechanism, in accordance with aspects of the present teachings.

FIG. 22 shows another exemplary system 450 for fixing rib bones. Fixation system 450 may include a bone plate 452 disposed on a rib bone 454 and having an integral fastener mechanism 456. The fastener mechanism may include a tie member 458, such as a belt or strap, that secures the bone plate to bone. The tie member may extend at least partially around the rib bone from a plate body 460 of the bone plate, for example, extending between opposing arms 464, 466 of a hook portion 468 of the plate body disposed adjacent opposing surfaces of the rib bone. Accordingly, the plate body and tie member collectively may extend completely around the rib bone.

The tie member may be part of a cable tie or "zip tie" mechanism that adjustably secures or cinches the bone plate around the rib bone. The cable tie mechanism may include a detent mechanism 470 formed cooperatively by the tie member and retainer 472 of plate body. The retainer may be defined by an aperture 474 having one or more body detents 476 created by the wall of the aperture. The tie member may include an array of cooperating tie detents 478, such as an array of ridges and/or depressions to form teeth for engagement with the body detents. The tie and/or body detents may be angled or biased to permit tightening motion of the tie member through aperture 474 in one direction, and to restrict loosening motion in the opposing direction. During installation of the bone plate, the tie member may be fed through aperture 474 and pulled tight. A suitable extension portion or end region 480 of the tie member, indicated in phantom, may be removed (e.g., cut or broken off) at any suitable time, generally after the bone plate is secured fully.

The cable tie mechanism may have any suitable relationship to the bone plate and plate body. For example, the cable tie mechanism may be a separate component that is secured around the bone plate and bone after the bone plate is installed on bone. If a separate component, the cable tie mechanism may be received in recesses or passages formed by the bone plate, or between projections of the bone plate, to restrict lateral slippage of the cable tie mechanism. In some embodiments, the cable tie mechanism may be partially or fully integral to the bone plate. For example, the tie member and plate body may be molded at the same time, such as out of a relatively flexible material, such as plastic and/or a bioresorbable material. In other examples, the tie member may be formed as a separate component and then attached to the plate body, such as via bonding, an adhesive, and/or fasteners, among others. The retainer portion of the cable tie that receives the tie member also may be formed as part of the plate body, or may be formed separately and then attached to the plate body or used as a separate component. The cable tie mechanism(s) may be part of a hook portion of a bone plate, may be spaced from the hook portion(s) of the bone plate, or may be included in, or used with, a bone plate having no hook portions. Furthermore, each bone plate may include and/or may be secured with any suitable number of cable tie mechanisms. In some examples, each hook portion of the bone plate may be secured with one or more corresponding cable tie mechanisms.

Bone plate 452 also or alternatively may include surface structure formed on an inner surface 482 to restrict slippage of the bone plate relative to bone before, during, and/or after the bone plate is secured by a fastener mechanism. The surface structure may include a projection(s) such as a prong(s) 484. The surface structure may be formed on the arm of a hook portion, such as on the distal (and/or proximal) arm of the hook portion, on the bridge region, and/or on the spanning portion, among others. Alternatively, or in addition, the surface structure may include one or more ridges, knobs, etc.

Figure 23:
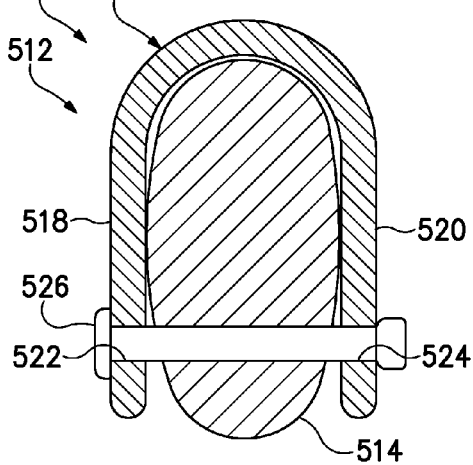
FIG. 23 is a sectional view of still another exemplary system for fixing rib bones, taken generally through a hook portion of a bone plate secured to a rib bone with a through rivet, in accordance with aspects of the present teachings.

FIG. 23 shows another exemplary system 510 for fixing rib bones. Fixation system 510 may include a bone plate 512 disposed on a rib bone 514 and having one or more hook portions 516 hooked onto the rib bone. Each hook portion may include arms 518, 520 of approximately equal (or unequal) length to produce or U-shaped (or J-shaped) hook portion. In any case, the arms may define at least one aligned pair of apertures 522, 524 for receiving a through rivet 526 that extends completely through the rib bone to secure the hook portion (and bone plate) to the rib bone.

Figure 24:
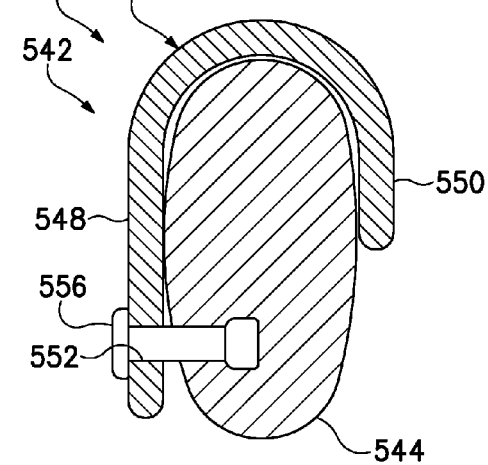
FIG. 24 is a sectional view of still yet another exemplary system for fixing rib bones, taken generally through a hook portion of a bone plate secured to a rib bone with a blind rivet, in accordance with aspects of the present teachings.

FIG. 24 shows another exemplary system 540 for fixing rib bones. Fixation system 540 may include a bone plate 542 disposed on a rib bone 544 and having one or more hook portions 546 hooked onto the rib bone. Each hook portion may include arms 548, 550 of unequal (or approximately equal) length to produce or J-shaped (or U-shaped) hook portion. In any case, proximal arm 548 may define at least one aperture 552 for receiving a blind rivet 556 that extends into but not completely through the rib bone to secure the hook portion (and bone plate) to the rib bone. Blind rivet 556

(and/or through rivet 526 of FIG. 23) may be formed of any suitable material, such as metal, plastic, and/or a bioresorbable material, among others.

Example 10

Exemplary Bone Plates Secured Via Sutures

This example describes exemplary bone plates suitable to be secured to bones, such as rib bones, via one or more sutures; see FIGS. 25-28.

Figure 25:
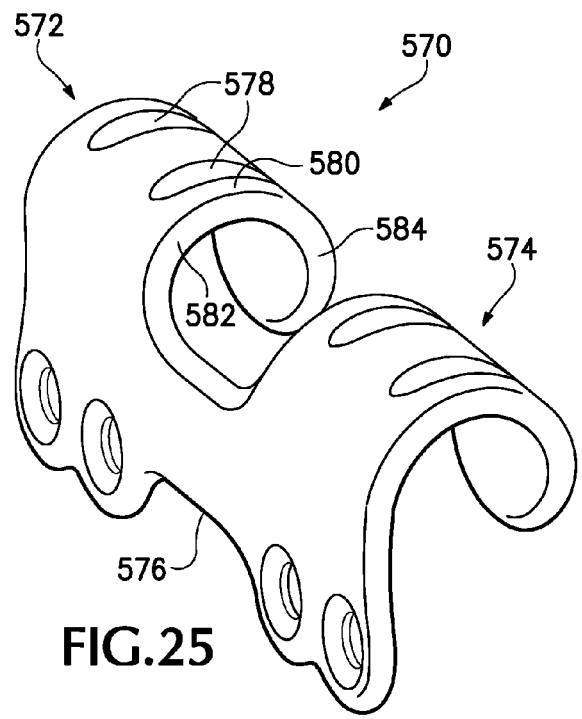
FIG. 25 is a view of a sixth embodiment of an exemplary bone plate for fixing rib bones, in accordance with aspects of the present teachings.

FIG. 25 shows an exemplary bone plate 570 for fixing a rib bone. Plate 570 may include a pair of hook portions 572, 574 connected and extending unilaterally from a spanning portion 576. Each hook portion may define one or more channels 578 for receiving a suture segment. For example, in the present illustration, each hook portion has a pair of channels. Each channel may extend through the plate, between inner and outer surfaces of the bone plate and/or may be or may include a depression (e.g., a notch) formed only in the outer surface and/or edge of the bone plate.

The channel may have any suitable position and orientation with respect its corresponding hook portion. For example, the channel may be disposed in a bridge region 580, generally between arms 582, 584 of the hook portion, near an apex of the hook portion. Alternatively, or in addition the channel may be disposed partially or exclusively in one or both of the arms. In some examples, one or more channels may be disposed partially or exclusively in the spanning portion of the bone plate. The channel may extend along a linear, angular, and/or curved path, among others. Furthermore, the channel may extend obliquely, parallel, and/or transversely (e.g., orthogonally as shown here) to a plane defined by the spanning portion of the bone plate.

Figure 26:
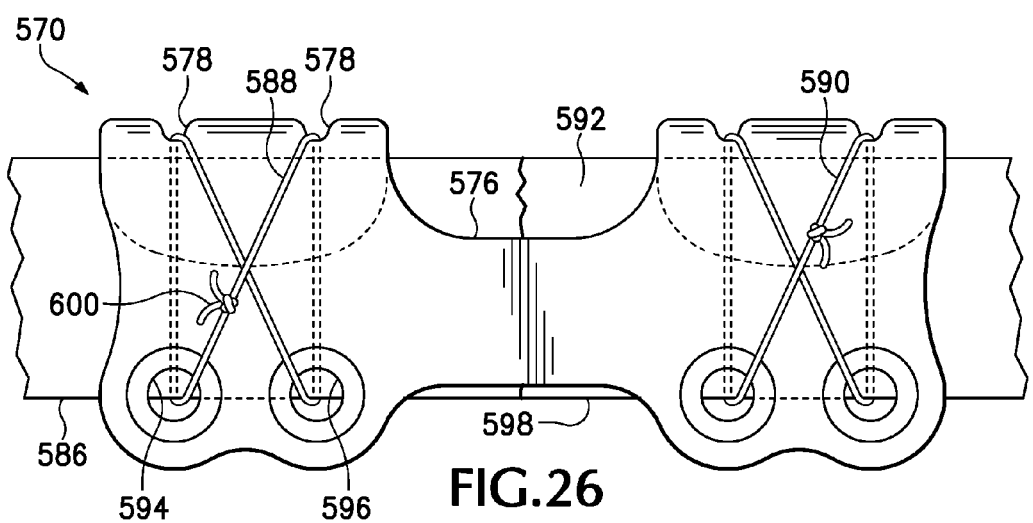
FIG. 26 is an elevation view of the bone plate of FIG. 25 with the bone plate secured to a rib bone with suture material, taken generally from outward of the rib bone, in accordance with aspects of the present teachings.

FIG. 26 shows bone plate 570 secured to a fractured rib bone 586 with a pair of sutures 588, 590. The bone plate may be positioned, for example, with the spanning portion 576 adjacent an outward surface 592 of the rib bone and extending axially along the rib bone. Each suture may extend through a pair of apertures 594, 596 defined by a proximal arm of the hook portion. Each aperture may be disposed at about the same level/height (along a superior-inferior axis) as inferior border 598 of the rib bone, or lower than this border, to enable threading the suture through each of the apertures. The suture may extend around the rib bone once, twice (as shown here), or more. Channels 578 may receive the suture and restrict slippage transverse of the channels (e.g., slippage axially along the bone plate). Each suture may be secured via a knot(s) 600 and/or any another suitable suture retainer.

Bone plate 570 (and/or any of the other bone plates described herein) and/or the sutures may be formed of any suitable material. In exemplary embodiments, each is formed of a bioresorbable material.

FIG. 27 shows another exemplary bone plate 620 for fixing rib bones with the bone plate secured to a rib bone 622 via one or more integral sutures 624. The bone plate may include a pair of hook portions 626, 627 with each hook portion connected to one or more sutures. For example, a distal arm 628 of the hook portion may be connected to a pair of sutures, indicated at 630, before the bone plate is installed on bone. The sutures may be attached during and/or after manufacture of the bone plate. For example, each suture may be partially embedded in the distal arm as the plate is being formed (e.g., as the plate is molded) and/or may be secured after the plate is formed via bonding, an adhesive, and/or a retention mechanism. The retention mechanism may structured, for example, such that an end of each suture extends through an aperture in the distal arm and engages the aperture wall via an enlarged end of the suture (e.g., formed by a knot or other anchor structure).

Bone plate 620 may be installed on a rib bone as follows. The bone plate may be hooked onto the rib bone with sutures 624, in an unsecured configuration, extending from the distal arms of the hook portions. The free ends of each suture pair then may be brought downward and forward around the inferior side of the bone and placed through a pair of apertures 632 in each hook portion. The ends may be tied together to form a knot 634 that restrains the suture ends and secures the bone plate onto the rib bone. In other embodiments, a single integral suture or a combination of integral sutures may extend diagonally and/or completely around the rib bone, among others, in a secured configuration.

FIG. 28 shows yet another exemplary bone plate 650 for fixing rib bones and configured to be secured to bone via one or more sutures. Bone plate 650 may be configured as a longer version of bone plate 570 (see FIGS. 25 and 26). In particular, plate 650 may include at least two hook portions 652, 653 connected by a spanning portion 654. The spanning portion may include one or more apertures 656 arranged to receive one or more sutures 658. The hook portions also may receive the same suture as the spanning portion or may receive distinct sutures 660 and 662, as shown here.

Apertures 656 may have any suitable disposition in the spanning portion. For example, the apertures may be obliquely disposed relative to one another, in an alternating lateral offset, to create a zigzag or staggered pattern of apertures. The spanning portion may have a uniform width or may widen at positions of the apertures, such as to produce tabs 660 that at least partially define the apertures.

Example 11

Exemplary Set of Bone Plates and Fasteners of Different Size

Figure 29:
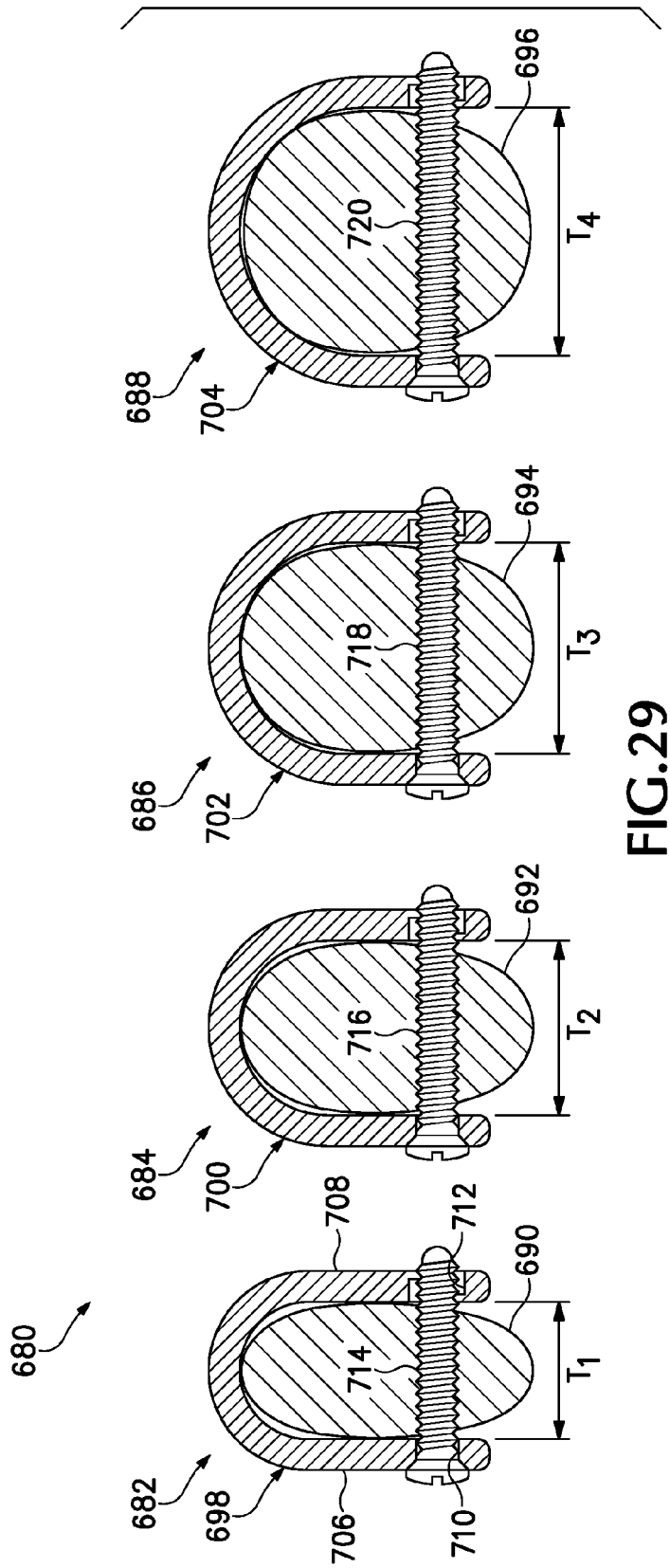
FIG. 29 is a cross-sectional view of an exemplary set of bone plates and corresponding fasteners secured to rib bones of different thickness, in accordance with aspects of the present teachings.

This example describes an exemplary set or kit 680 including bone plates 682-688 sized to fit respectively onto rib bones 690-696 of different thickness ($T_1$ to $T_4$); see FIG. 29.

Each bone plate may have one or more hook portions 698-704, shown here in cross section. The hook portions of each bone plate may have a distinct size relative to other bone plates of the set. For example, a proximal arm 706 and a distal arm 708 of a hook portion (or of each hook portion) of one bone plate may be separated by a different spacing (distance) than the hook portion(s) in one or more other bone plates of the set. Accordingly, a surgeon may select a bone plate from the set according to the thickness of a target rib bone onto which the bone plate is to be installed. In exemplary embodiments, the hook portions may have an arm-to-arm spacing of about 5-20 millimeters, with particular exemplary spacings of 8, 10, 12, and/or 14 millimeters, corresponding respectively to small, medium, large, and extra large rib bones. Selection of a suitable size of bone plate may be based on measuring the thickness of the target rib bone, to, for example, allow selection of a size of bone plate that is closest to the measured thickness of the rib bone. Alternatively, or in addition, selection may be based on trial fitting of bone plates onto the target rib bone to find the best fit.

The hook portions may have any suitable arm length(s). For example, the arms may be about the same length within each hook portion and/or between hook portions of different size. Alternatively, the arms may be of different length within a hook portion (e.g., to produce a J-shaped hook portion)

and/or between hook portions of different size (e.g., longer arms for hook portions sized for thicker and/or wider rib bones).

The hook portions may have any suitable arrangement of apertures. For example, each hook portion may define at least a pair of aligned apertures 710, 712 for receiving a fastener such as bone screws 714-720, shown here. The bone screws may have different lengths that correspond to the different sizes of the hook portions. In particular, set 680 may include different bone screws (or other fasteners) that are about the same length (e.g., slightly longer) as the arm-to-arm spacings of the various hook portions. Accordingly, during plate installation, a surgeon may select a fastener(s) that corresponds in size (length) to the size of bone plate (hook portion) selected. Alternatively, or in addition, the surgeon may select the same size (length) of fastener for each size of bone plate, such as when the fastener is placed into, but not through, bone.

Example 12

Selected Embodiments

This section describes selected embodiments of the present teachings, presented as a series of indexed paragraphs.

1. A device for fixing bone, comprising: a bone plate including a plate body and at least one tie member connected integrally to the plate body and configured to secure the plate body to bone.

2. The device of paragraph 1, wherein the at least one tie member is a separate component attached nonremovably to the plate body.

3. The device of paragraph 2, wherein the at least one tie member and the plate body are part of the same monolithic structure.

4. The device of paragraph 1, wherein the at least one tie member includes a line of monofilament or multi-filament construction.

5. The device of paragraph 1, wherein the at least one tie member is at least substantially bioresorbable.

6. The device of paragraph 1, wherein the at least one tie member is included in a cable tie mechanism.

7. The device of paragraph 6, wherein the cable tie mechanism includes a retainer for receiving the at least one tie member, and wherein the retainer and the plate body are part of the same monolithic structure.

8. The device of paragraph 1, wherein the plate body include at least one hook portion having opposing arms, and wherein the at least one tie member is connected integrally to the plate body via one of the opposing arms.

9. The device of paragraph 8, wherein the other opposing arm defines an opening structured to receive the at least one tie member.

10. The device of paragraph 9, wherein the at least one tie member includes a pair of free ends, and wherein the other opposing arm defines at least a pair of openings for receiving the pair of free ends.

11. A method of fixing bone, comprising: (A) selecting a bone plate including a plate body and at least one tie member connected integrally to the plate body; (B) placing the bone plate onto a bone; and (C) securing the bone plate to the bone via the at least one tie member.

12. The method of paragraph 11, wherein the step of securing includes a step of disposing the tie member such that the plate body and tie member collectively extend completely around the bone.

13. The method of paragraph 11, wherein the plate body has opposing sides disposed laterally on the bone plate, wherein the tie member is connected integrally to the plate body adjacent one of the sides, and wherein the step of securing includes a step of engaging the tie member with the plate body adjacent the other opposing side.

14. The method of paragraph 11, wherein the step of securing includes a step of forming a knot in the at least one tie member.

15. The method of paragraph 11, wherein the step of securing includes a step of engaging the at least one tie member with a retainer that selectively permits tightening and restricts loosening of the at least one tie member.

16. The method of paragraph 11, further comprising a step of removing an end portion of the at least one tie member after the step of securing.

17. The method of paragraph 11, wherein the plate body includes a hook portion having opposing arms, wherein the step of placing includes a step of placing the hook portion onto a bone such that the arms are disposed adjacent opposing surfaces of the bone, and wherein the step of securing includes a step of spanning the arms with the at least one tie member.

18. The method of paragraph 11, wherein the step of placing the bone plate includes a step of placing the bone plate onto a rib bone.

19. The method of paragraph 11, wherein the step of selecting a bone plate includes a step of selecting a bone plate including a tie member for a cable tie mechanism.

20. A device for fixing a rib bone, comprising: a bone plate including a spanning portion and an exclusively unilateral arrangement of hook portions each configured to be hooked onto a rib bone and connected to the spanning portion in a spaced relation along the spanning portion when the bone plate is installed on a rib bone with the spanning portion disposed adjacent an outward surface of the rib bone.

21. A device for fixing a rib bone, comprising: a bone plate including a spanning portion defining a plane and a long axis and also including an exclusively unilateral arrangement of hook portions extending from the spanning portion such that the bone plate is configured to be hooked onto a rib bone by translational motion of the bone plate transverse to the long axis and generally parallel to the plane.

22. A device for fixing a rib bone, comprising: a bone plate including a spanning portion having opposing edges and also including at least a pair of plate-like hook portions configured to hook onto a rib bone with the spanning portion disposed adjacent an outward surface of the rib bone, every hook portion of the bone plate extending from the spanning portion at least substantially from adjacent only one of the opposing edges.

23. A device for fixing a rib bone, comprising: a bone plate including a spanning portion connected to at least two hook portions configured hook onto a rib bone with the spanning portion adjacent an outward surface of the rib bone, every hook portion of the bone plate extending away from the spanning portion in the same general rotational direction.

24. A device for fixing a rib bone, comprising: a bone plate including a spanning portion and a unilateral arrangement of hook portions extending from the spanning portion such that the bone plate is configured to be hooked onto a rib bone by translational motion of the bone plate from superior to the rib bone.

25. A method of fixing a rib bone, comprising: (A) selecting a rib bone with a discontinuity and opposing outward and inward surfaces flanked by opposing superior and inferior surfaces; (B) selecting a bone plate; and (C) securing the bone plate to the rib bone such that the bone plate spans the discontinuity and the bone plate wraps only partially around the rib bone, the bone plate extending from adjacent the outward surface to adjacent the inward surface exclusively via the superior surface.

26. A method of fixing a rib bone, comprising: (A) selecting a rib bone with a discontinuity and having opposing outward and inward surfaces flanked by opposing superior and inferior surfaces; (B) selecting a bone plate; and (C) placing the bone plate onto the superior surface of the rib bone via a superior approach such that the bone plate spans the discontinuity and the bone plate wraps only partially around the rib bone by extending from adjacent the outward surface to adjacent the inward surface.

27. A device for fixing a rib bone, comprising: a bone plate structured to be installed on a rib bone and including a spanning portion having opposing edges and also including one or more hook portions, every hook portion of the bone plate extending selectively from adjacent the same one of the opposing edges and around the rib bone at least to an opposing side of the rib bone when the spanning portion is disposed adjacent an outward surface of the rib bone with the opposing edges extending along the rib bone.

28. A device for fixing a rib bone, comprising: a bone plate structured to be installed on a rib bone and including a spanning portion and one or more hook portions, every hook portion of the bone plate extending from the spanning portion to follow only a superior path to an opposing side of the rib bone when the spanning portion is disposed axially on the rib bone adjacent an outward surface of the rib bone.

29. A device for fixing a rib bone, comprising: a bone plate including a spanning portion and at least one hook portion connected to the spanning portion and configured to extend away from the spanning portion around a rib bone at least to an opposing side of the rib bone when the bone plate is installed on the rib bone, the bone plate being configured to permit placement of every hook portion of the bone plate on the rib bone from superior to the rib bone and such that the spanning portion is disposed axially adjacent an outward surface of the rib bone.

30. A device for fixing a rib bone, comprising: a bone plate including a spanning portion configured to be disposed axially on a rib bone and also including at least one hook portion, every hook portion of the bone plate extending asymmetrically from the spanning portion in the same rotational direction around the rib bone to an opposing side of the rib bone, when the spanning portion is disposed axially adjacent an outward surface of the rib bone.

31. A device for fixing a rib bone, comprising: a bone plate including a spanning portion configured to be disposed axially on a rib bone and at least one hook portion, the bone plate being configured to received on the rib bone by translational motion from a position superior to the rib bone such that every hook portion of the bone plate opposes inward, outward, and superior surfaces of the rib bone and such that the spanning portion is disposed axially adjacent an outward surface of the rib bone.

32. A bone plate for fixing a rib bone, comprising: (A) a spanning portion configured to be disposed axially on a rib bone; and (B) a plurality of hook portions connected to the spanning portion, every hook portion of the bone plate extending asymmetrically from the spanning portion in the same general direction around the rib bone to an opposing side of the rib bone, when the spanning portion is disposed axially on the rib bone.

33. A bone plate for fixing a rib bone, comprising: (A) a spanning portion; and (B) a plurality of hook portions configured to extend away from the spanning portion around a rib bone to an opposing side of the rib bone when the bone plate is installed on the rib bone with the spanning portion disposed axially on the rib bone, every hook portion of the bone plate being configured to extend around the rib bone from the spanning portion in the same general direction.

34. A device for fixing a rib bone, comprising: a unitary bone plate including a spanning portion defining a central axis and configured to be disposed axially on a rib bone, and at least one hook portion configured to extend away from the spanning portion around a rib bone to an opposing side of the rib bone when the bone plate is installed on the rib bone, every hook portion of the unitary bone plate extending asymmetrically from the central axis and in the same general direction such that no hook portion obstructs placement of the bone plate onto the rib bone from a position superior to the rib bone.

35. A device for fixing a rib bone, comprising: a bone plate including a spanning portion and at least one hook portion connected to the spanning portion and configured to extend away from the spanning portion around a rib bone to an opposing side of the rib bone when the bone plate is installed on the rib bone, every hook portion of the bone plate extending in the same general direction from the spanning portion to permit translational placement of the spanning portion onto an outward surface of the rib bone from a position directly superior to the rib bone.

36. A device for fixing a rib bone, comprising: a unitary bone plate including a spanning portion and at least one hook portion configured to extend away from the spanning portion around a rib bone to an opposing side of the rib bone when the bone plate is installed on the rib bone, the bone plate being configured to permit receiving every hook portion of the bone plate on the rib bone from superior to the rib bone for placement of the spanning portion adjacent an outward surface of the rib bone.

37. The bone plate of any of the preceding paragraphs, wherein the bone plate is unitary.

38. The bone plate of any of the preceding paragraphs, wherein the bone plate is formed of metal.

39. The bone plate of any of the preceding paragraphs, wherein the bone plate is formed of a bioresorbable material.

40. The bone plate of any of the preceding paragraphs, further comprising one or more hook components configured to be connected to the bone plate such that each hook component extends asymmetrically from the spanning portion in the same general direction around the rib bone as the one or more hook portions when the bone plate and the one or more hook components are assembled on the rib bone.

41. The bone plate of paragraph 40, the spanning portion having opposing inner and outer surfaces, wherein each hook component is configured to flank the rib bone and the spanning portion, in engagement with the outer surface of the spanning portion.

42. The device of paragraph 41, wherein the bone plate and each hook component defines a pair apertures configured to be aligned when the bone plate and the hook component are installed on the rib bone.

43. The bone plate of any of the preceding paragraphs, wherein each hook portion defines at least one aperture.

44. The device of claim 43, wherein each hook portion defines a pair of aligned apertures configured to receive a fastener extending through the rib bone and between the pair of aligned apertures when the bone plate is installed on the rib bone.

45. The bone plate of any of the preceding paragraphs, wherein the bone plate includes at least a pair of hook portions that are unitary with the spanning portion and spaced from one another along the spanning portion.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A device for fixing bone, comprising:
    a plate member having an outer face, an inner face, and a pair of edge surface regions arranged opposite each other and each being contiguous with the outer and inner faces and configured to be disposed adjacent a same first side of a same bone;
    a pair of hook members each projecting from a position adjacent the same edge surface region of the plate member, to form a space to receive the bone between the plate member and each of the hook members with each hook member extending to a second side of the bone opposite the first side, wherein the plate member and a hook member define first and second aligned apertures; and
    a fastener configured to extend from the first aperture, through the bone, and into locked engagement with the second aperture.

2. The device of claim 1, wherein each hook member alone or in combination with the plate member forms a clip portion that is at least generally U-shaped.

3. The device of claim 1, wherein the edge surface regions are formed by a top edge and a bottom edge of the plate member.

4. The device of claim 3, wherein the hook members project from positions adjacent the top edge of the plate member.

5. The device of claim 1, wherein the hook members are continuous with the plate member.

6. The device of claim 1, wherein a hook member is provided by an at least generally U-shaped clip portion that is discrete from the plate member.

7. The device of claim 1, wherein the second aperture is a slot having a linear ridge, and wherein the fastener has an external thread configured to engage the linear ridge to produce the locked engagement.

8. A device for fixing bone, comprising:
    a plate member having a top edge and a bottom edge each configured to be disposed adjacent a same first side of a same bone;
    a pair of hook members each projecting from a position adjacent the top edge of the plate member, to form a space to receive a same bone between the plate member and both hook members with each hook member extending to a second side of the bone opposite the first side and such that the device does not extend on the bone to the second side of the bone intermediate the hook members, wherein the plate member and an end of a hook member define first and second aligned apertures; and
    a fastener configured to extend from the first aperture, through the bone, and into locked engagement with the second aperture.

9. The device of claim 8, wherein each hook member alone or in combination with the plate member forms a clip portion that is at least generally U-shaped.

10. The device of claim 8, wherein a hook member is provided by an at least generally U-shaped clip portion that is discrete from the plate member.

11. The device of claim 8, wherein at least one of the hook members is continuous with the plate member.

12. The device of claim 11, wherein both of the hook members are continuous with the plate member.

13. The device of claim 8, wherein a hook member is discrete from the plate member.

14. The device of claim 8, wherein the hook members are a first hook member and a second hook member, wherein the second aperture is defined by the first hook member, and wherein the plate member and an end of the second hook member define third and fourth aligned apertures configured to receive a fastener in locked engagement with the fourth aperture.

15. A device for fixing bone, comprising:
    a plate member having a pair of edges arranged opposite each other;
    a pair of hook members projecting from respective spaced positions adjacent the same edge of the plate, to form a space to receive a same bone between the plate member and each of the hook members, wherein each hook member alone or in combination with the plate member forms a clip portion that is at least generally U-shaped, wherein the plate member and a hook member define a pair of aligned apertures, and wherein the device is at least generally U-shaped in transverse cross section at each clip portion but not intermediate the clip portions; and
    a fastener configured to extend from one of the apertures, through the bone, and into locked engagement with the other aperture.

16. The device of claim 15, wherein the edges are a top edge and a bottom edge of the plate member.

17. The device of claim 16, wherein the hook members project from adjacent the top edge of the plate member.

18. The device of claim 15, wherein the hook members are continuous with the plate member.

19. The device of claim 15, wherein a hook member is provided by a clip portion that is discrete from the plate member.

* * * * *